United States Patent [19]

Takabe et al.

[11] Patent Number: 5,403,816

[45] Date of Patent: * Apr. 4, 1995

[54] PICOLINIC ACID DERIVATIVE AND HERBICIDAL COMPOSITION

[75] Inventors: Fumiaki Takabe; Yoshihiro Saito; Masatoshi Tamaru; Shigehiko Tachikawa; Ryo Hanai, all of Shizuoka, Japan

[73] Assignees: Kumiai Chemical Industry Co., Ltd.; Ihara Chemical Industry Co., Ltd., both of Tokyo, Japan

[*] Notice: The portion of the term of this patent subsequent to Feb. 21, 2012 has been disclaimed.

[21] Appl. No.: 48,516

[22] Filed: Apr. 20, 1993

Related U.S. Application Data

[63] Continuation-in-part of Ser. No. 960,844, Oct. 14, 1992, Pat. No. 5,391,537, which is a continuation-in-part of Ser. No. 842,163, Mar. 31, 1992, abandoned.

[30] Foreign Application Priority Data

Oct. 25, 1990 [JP] Japan .................................. 2-288180
Apr. 23, 1992 [JP] Japan .................................. 4-129376

[51] Int. Cl.$^6$ ................. C07D 401/12; C07D 401/06; A01N 43/54
[52] U.S. Cl. ..................................... 504/243; 544/123; 544/300; 544/319; 544/96; 540/601; 540/481; 504/219; 504/209; 504/225; 504/223
[58] Field of Search ............... 504/243, 219, 209, 225, 504/223; 544/300, 123, 319, 96; 540/601, 481

[56] References Cited

U.S. PATENT DOCUMENTS

| 4,832,729 | 5/1989 | Shigematsu et al. ............... 544/300 |
| 4,931,087 | 6/1990 | Shigematsu et al. ............... 544/218 |
| 5,015,285 | 5/1991 | Rheinheimer ...................... 544/310 |

FOREIGN PATENT DOCUMENTS

| 0249707 | 12/1987 | European Pat. Off. . |
| 0249708 | 12/1987 | European Pat. Off. . |
| 0346789 | 12/1989 | European Pat. Off. . |
| 0360163 | 3/1990 | European Pat. Off. . |
| 0461079 | 12/1991 | European Pat. Off. . |
| 0472925 | 3/1992 | European Pat. Off. . |
| 0507962 | 10/1992 | European Pat. Off. . |
| 0521407 | 1/1993 | European Pat. Off. . |
| WO9110653 | 7/1991 | WIPO . |

Primary Examiner—John M. Ford
Attorney, Agent, or Firm—Oblon, Spivak, McClelland, Maier, & Neustadt

[57] ABSTRACT

3-Pyrimidinyloxy-substituted picolinic acid derivatives of the formula

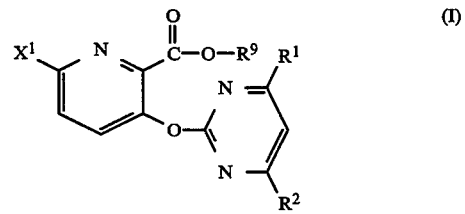

and their salts are useful as herbicides against annual and perennial gramineous and broadleaf weeds while exhibiting low phytotoxicity to desired crop plants.

8 Claims, No Drawings

PICOLINIC ACID DERIVATIVE AND HERBICIDAL COMPOSITION

This application is a continuation-in-part of application Ser. No. 07/960,844, filed on Oct. 14, 1992, now U.S. Pat. No. 5,391,537, which is a continuation-in-part of application Ser. No. 07/842,163, filed Mar. 31, 1992, now abandoned, which was filed as International Application No. PCT/JP91/01459, on Oct. 25, 1991.

BACKGROUND OF THE INVENTION

1. FIELD OF THE INVENTION

The present invention relates to a picolinic acid derivative and a salt thereof, and a herbicidal composition containing the same as an active ingredient, which is applicable to a paddy field, an upland filed and a non-agricultural land.

2. DISCUSSION OF BACKGROUND

As a herbicide having a structure similar to the compound of the present invention, a 3-(4,6-dimethoxypirimidin-2-yl)oxypicolinic acid derivative has been known (Japanese Unexamined Patent Publication No. 121973/1990). This publication discloses a picolinic acid type (2-pyridine-carboxylic acid) structure and an isonicotinic acid type (4-pyridine-carboxylic acid) structure as a compound having a pyridine ring. However, this publication does not disclose a compound having a substituent on the pyridine ring, like the compound of the present invention. Accordingly, there is no specific disclosure or suggestion of the herbicidal effects of such a compound.

Further, it is also known that a 2-sulfoneaminopyrimidine derivative has herbicidal activities (Japanese Unexamined Patent Publication No. 149567/1990). However, in this case, a large dose is required to control various weeds simultaneously, and its herbicidal effects are not yet satisfactory.

Furthermore, a similar patent publication (WO-9207846-Al) discloses herbicidal effects of an amino group derivative at the 6-position of picolinic acid. However, there is no specific description about the safety of the compound to crop plants, and the herbicidal effects are not satisfactory particularly to control weeds in an agricultural field.

In recent years, a number of herbicides have been developed and practically used, and they have contributed to the saving of energy for the agricultural operations and to the improvement of the production efficiency. However, in their practical use, such herbicides have various problems with respect to the herbicidal effects and the safety to the crop plants. For example, perennial weeds such as Johnsongrass are widely distributed throughout agricultural fields in the world and regarded as weeds which are very difficult to control. Under the circumstances, it is desired to develop an improved herbicide.

SUMMARY OF THE INVENTION

The present inventors have conducted extensive research on picolinic acid derivatives with an aim to solve the above-mentioned problems and as a result, have found that a picolinic acid derivative substituted by a pirimidinyloxy group exhibits excellent herbicidal effects against annual and perennial gramineous and broadleaf weeds, and at the same time, it is highly safe to crop plants such as corn. It has been also found that the picolinic acid derivative exhibits excellent herbicidal effects at a low dose especially against annual gramineous weeds, and at the same time, adequate herbicidal effects can be obtained also against perennial weeds such as Johnsongrass. The present invention has been accomplished on the basis of these discoveries.

Thus, the present invention provides a herbicide containing as an active ingredient a picolinic acid derivative of the formula:

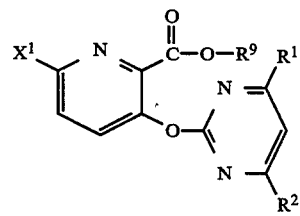

(I)

wherein each of $R^1$ and $R^2$ is an alkoxy group, $X^1$ is a group of the formula

wherein $R^3$ is a hydrogen atom, an alkyl group, a haloalkyl group, an alkoxyalkyl group, an alkenyl group, an alkynyl group, an alkylcarbonyl group, a benzyloxycarbonyl group or a phenylsulfonyl group, and $R^4$ is a haloalkyl group, an alkoxyalkyl group, an alkoxyalkyloxyalkyl group, an alkoxycarbonylalkyl group, a benzyloxyalkyl group, an alkyloxyoxyalkyl group, a phenoxyalkyl group, a dialkylaminoalkyl group, a cyanoalkyl group, an alkoxy group, a cycloalkyl group, an alkenyl group (which may be substituted at one or more positions by a halogen atom or a cyano group), an alkynyl group, a phenylalkyl group (which may be the same or different, and substituted at one or more positions by a halogen atom, an alkyl group, an alkoxy group, a nitro group or a cyano group), a cycloalkylcarbonyl group, a haloalkylcarbonyl group, an alkoxyalkylcarbonyl group, a cyanoalkylcarbonyl group, a phenoxyalkylcarbonyl group, a phenylalkylcarbonyl group, a halophenylalkylcarbonyl group, a benzoyl group (which is substituted by an alkyl group, a haloalkyl group, a halogen atom, an alkoxy group, a cyano group or a nitro group), a furylcarbonyl group, a pyridylcarbonyl group, a pryyolylcarbonyl group, a thienylcarbonyl group, an alkenylcarbonyl group, a phenylalkenylcarbonyl group, a hydroxycarbonylalkenylcarbonyl group, an alkoxycarbonylalkylcarbonyl group, an alkoxyalkoxycarbonyl group, a monoalkylaminocarbonyl group, a dialkylaminocarbonyl group, a phenylaminocarbonyl group, a benzylaminocarbonyl group, a halobenzylaminocarbonyl group, an alkoxycarbonyl group, a haloalkoxycarbonyl group, a benzyloxycarbonyl group, an alkenyloxycarbonyl group, an alkynyloxycarbonyl group, an alkylsulfonyl group, a haloalkylsulfonyl group, a benzylsulfonyl group which may be substituted by an alkoxycarbonyl group, a phenylsulfonyl group which may be substituted by an alkoxycarbonyl group, a halopheylsulfonyl group, an alkyl(thiocarbonyl) group, a haloalkyl(thiocarbonyl) group, a benzyl(thiocarbonyl) group, a halobenzyl(thiocarbonyl) group, an alkenyl(thiocarbonyl) group, an alkynyl(thiocarbonyl) group which may be substituted by a cyano group, an alkylamino(thiocarbonyl) group, a phenylamino(thiocarbonyl) group, a dialkylamino(thiocarbonyl) group, a benzyloxy group or a group of the formula

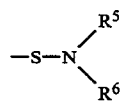

wherein each of $R^5$ and $R^6$ which may be the same or different, is a hydrogen atom, an alkyl group or an alkoxycarbonyl group, or $R^5$ and $R^6$ form together with the adjacent nitrogen atom a morpholino group, or $R^3$ and $R^4$ form together with the adjacent nitrogen atom, an azido group, an isothiocyanate group, a phthalimide group, a maleimide group, a succinimido group, a pyrrolidinyl group, a piperidino group, a pyrrolyl group, a morpholino group, a group of the formula

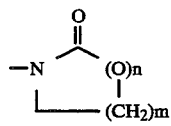

wherein n is 0 or 1, and m is 1 or 2, or a group of the formula

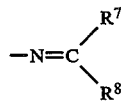

wherein each of $R^7$ and $R^8$ which may be the same or different, is a hydrogen atom, an alkyl group, a dialkylamino group, an amino group, an alkylthio group, a phenyl group or a benzyl group, and $R^9$ is a hydrogen atom, an alkyl group, an alkenyl group, a benzyl group, an alkali metal atom, an alkaline earth metal atom or an organic amine cation; or a salt thereof.

Further, the present invention provides a herbicide containing as an active ingredient a picolinic acid derivative of the formula:

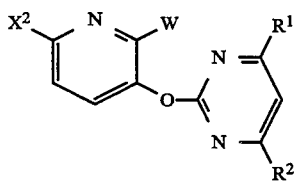

wherein each of $R^1$ and $R^2$ is an alkoxy group, $X^2$ is an amino group, an alkylamino group or a dialkylamino group, and W is $COOR^{10}$, $COSR^{11}$ or

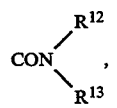

wherein $R^{10}$ is a phenyl group (which may be substituted by a halogen atom or a methyl group), a benzyloxyalkyl group, an alkylideneamino group, a cycloalkylideneamino group or a dialkylamino group, $R^{11}$ is an alkyl group or a phenyl group, and each of $R^{12}$ and $R^{13}$ which may be the same or different, is a hydrogen atom, an alkylsulfonyl group, an alkoxyalkyl group, an alkyl group, a benzyloxy group or an alkoxy group, or $R^{12}$ and $R^{13}$ form together with the adjacent nitrogen atom, an imidazolyl group; or a salt thereof.

Furthermore, the present invention provides a herbicide containing as an active ingredient a picolinic acid derivative of the formula:

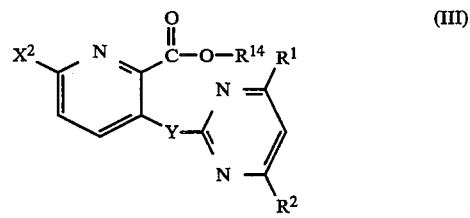

wherein each of $R^1$ and $R^2$ is an alkoxy group, $X^2$ is an amino group, an alkylamino group or a dialkylamino group, Y is a methylene group which may be substituted by a cyano group, or a carbonyl group, and $R^{14}$ is a hydrogen atom or an alkyl group; or a salt thereof.

Still further, the present invention provides a herbicide containing as an active ingredient a picolinic acid derivative of the formula:

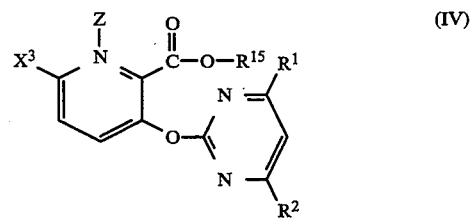

wherein each of $R^1$ and $R^2$ is an alkoxy group, $X^3$ is a dialkylamino group, Z is a group of the formula $R^+ \cdot A^-$ wherein $R^+$ is a cation selected from the group consisting of an alkyl group, an acyl group and an alkylsulfonyl group, and $A^-$ is an anion of the conjugate base, and $R^{15}$ is an alkyl group; or a salt thereof.

DETAILED DESCRIPTION OF THE PREFERRED EMBODIMENTS

Now, preferred examples of the substituents will be given. The alkyl and alkoxy groups may, for example, be $C_{1-5}$ linear or branched alkyl and alkoxy groups. The alkenyl and alkynyl groups may, for example, be $C_{2-6}$ alkenyl and alkynyl groups. The cycloalkyl group may, for example, be a $C_{3-6}$ cycloalkyl group. The alkylideneamino group may, for example, be a $C_{3-12}$ alkylideneamino group. The cycloalkylideneamino group may, for example, be a $C_{3-8}$ cycloalkylideneamino group. The acyl group may, for example, be a $C_{2-8}$ acyl group. The halogen atom may, for example, be a chlorine atom, a fluorine atom, a bromine atom or an iodine atom.

Now, specific compounds of the present invention will be given in Tables 1 to 5. The compound Nos. will be referred to in the subsequent description. In the Tables, D.P. means the decomposition point.

TABLE 1
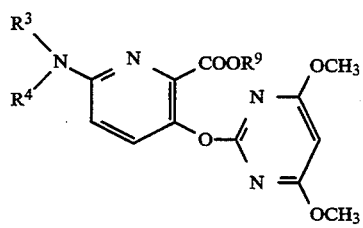
| Comp. No. | $R^3$ | $R^4$ | $R^9$ | m.p. (°C.) or $n_D^{20}$ |
|---|---|---|---|---|
| 1 | $C_2H_4Cl$ | $C_2H_4Cl$ | $CH_3$ | |
| 2 | $C_2H_4Cl$ | $C_2H_4Cl$ | H | |
| 3 | $CH_3$ | $C_2H_4CN$ | $CH_3$ | |
| 4 | $CH_3$ | $C_2H_4CN$ | H | |
| 5 | $CH_3$ | $C_2H_4F$ | $CH_3$ | |
| 6 | $CH_3$ | $C_2H_4F$ | H | |
| 7 | $CH_3$ | $C_2H_4O$-Ph | $CH_3$ | |
| 8 | $CH_3$ | $C_2H_4O$-Ph | H | |
| 9 | $CH_3$ | $C_3H_6F$ | $CH_3$ | |
| 10 | $CH_3$ | $C_3H_6F$ | H | |
| 11 | H | cyclopentyl | $CH_3$ | |
| 12 | H | cyclopentyl | H | |
| 13 | $CH_3$ | cyclopentyl | $CH_3$ | 72–73.5 |
| 14 | $CH_3$ | cyclopentyl | H | 139–140 |
| 15 | H | cyclohexyl | $CH_3$ | 167–168 |
| 16 | H | cyclohexyl | H | 182–184 |
| 17 | $CH_3$ | cyclohexyl | $C_4H_9$-i | 1.5478 |

TABLE 1-continued
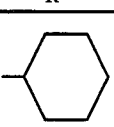
| Comp. No. | R³ | R⁴ | R⁹ | m.p. (°C.) or $n_D^{20}$ |
|---|---|---|---|---|
| 18 | CH₃ | cyclohexyl | CH₂–phenyl | Unmeasurable |
| 19 | CH₃ | cyclohexyl | CH₂CH=CH₂ | 1.5550 |
| 20 | CH₃ | cyclohexyl | CH₃ | 116–117.15 |
| 21 | CH₃ | cyclohexyl | H | 144–147 |
| 22 | CH₃ | CF₃ | CH₃ | |
| 23 | CH₃ | CF₃ | H | |
| 24 | H | CH₂–phenyl | CH₃ | 104–105 |
| 25 | H | CH₂–phenyl | H | 176–178 |
| 26 | CH₃ | CH₂–phenyl | CH₃ | 73–75 |
| 27 | H | CH₂–(4-CH₃-phenyl) | CH₃ | |
| 28 | H | CH₂–(4-CH₃-phenyl) | H | |
| 29 | CH₃ | CH₂–(4-Cl-phenyl) | CH₃ | |
| 30 | CH₃ | CH₂–(4-Cl-phenyl) | H | |

TABLE 1-continued

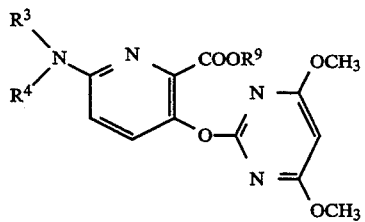

| Comp. No. | $R^3$ | $R^4$ | $R^9$ | m.p. (°C.) or $n_D^{20}$ |
|---|---|---|---|---|
| 31 | $CH_3$ | 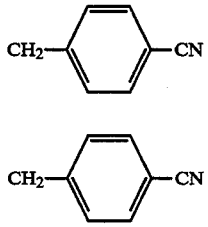 $CH_2$—⟨⟩—CN | $CH_3$ | |
| 32 | $CH_3$ | 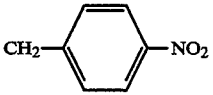 $CH_2$—⟨⟩—CN | H | |
| 33 | H | 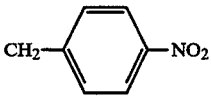 $CH_2$—⟨⟩—$NO_2$ | $CH_3$ | |
| 34 | H |  $CH_2$—⟨⟩—$NO_2$ | H | |
| 35 | H | 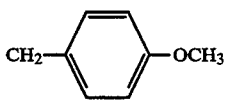 $CH_2$—⟨⟩—$OCH_3$ | $CH_3$ | |
| 36 | H | 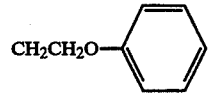 $CH_2$—⟨⟩—$OCH_3$ | H | |
| 37 | $CH_3$ | $CH_2C(Cl)=CHCl$ | $CH_3$ | |
| 38 | $CH_3$ | $CH_2C(Cl)=CHCl$ | H | |
| 39 | $CH_2C\equiv CH$ | $CH_2C\equiv CH$ | $CH_3$ | |
| 40 | $CH_2C\equiv CH$ | $CH_2C\equiv CH$ | H | 137–139 |
| 41 | H | $CH_2C\equiv CH$ | $CH_3$ | 101–102 |
| 42 | H | $CH_2C\equiv CH$ | H | 110–112 |
| 43 | $CH_3$ | $CH_2C\equiv CH$ | $CH_3$ | 121–123 |
| 44 | $CH_3$ | $CH_2C\equiv CH$ | H | 139–140 |
| 45 | $CH_3$ | $CH_2CF_3$ | $CH_3$ | |
| 46 | $CH_3$ | $CH_2CF_3$ | H | |
| 47 | $CH_3$ | $CH_2CH=C(Cl)_2$ | $CH_3$ | |
| 48 | $CH_3$ | $CH_2CH=C(Cl)_2$ | H | |
| 49 | H | $CH_2CH=(CH_3)_2$ | H | 139–143 |
| 50 | $CH_2CH=CH_2$ | $CH_2CH=CH_2$ | $CH_3$ | 1.5535 |
| 51 | $CH_2CH=CH_2$ | $CH_2CH=CH_2$ | H | 94–97 |
| 52 | H | $CH_2CH=CH_2$ | $CH_3$ | 109–110 |
| 53 | H | $CH_2CH=CH_2$ | H | 157–159 |
| 54 | $CH_3$ | $CH_2CH=CH_2$ | $CH_3$ | 110–112 |
| 55 | $CH_3$ | $CH_2CH=CH_2$ | H | 97–98 |
| 56 | H | $CH_2CH=CHCH_3$ | $CH_3$ | 82–85 |
| 57 | H | $CH_2CH=CHCH_3$ | H | 160–163 |
| 58 | $CH_3$ | $CH_2CH=CHCH_3$ | $CH_3$ | |
| 59 | $CH_3$ | $CH_2CH=CHCH_3$ | H | |
| 60 | $CH_3$ | $CH_2CH=CHCN$ | $CH_3$ | |
| 61 | $CH_3$ | $CH_2CH=CHCN$ | H | |
| 62 | H | $CH_2CH_2O$—⟨⟩ | H | 170–175 |

TABLE 1-continued

[Structure: pyridine with R³R⁴N- group, COOR⁹, and O-linked pyrimidine bearing two OCH₃ groups]

| Comp. No. | R³ | R⁴ | R⁹ | m.p. (°C.) or $n_D^{20}$ |
|---|---|---|---|---|
| 63 | COOCH₂–C₆H₅ | CH₂CH₂O–C₆H₅ | CH₃ | Unmeasurable |
| 64 | H | CH₂CH₂O–C₆H₅ | CH₃ | 1.5682 |
| 65 | H | CH₂CH₂OCH₃ | CH₃ | 1.5373 |
| 66 | CH₃ | CH₂CN | CH₃ | |
| 67 | CH₃ | CH₂CN | H | |
| 68 | H | CH₂COOCH₃ | CH₃ | 165–168 |
| 69 | H | CH₂COOC₂H₅ | CH₃ | 95–96 |
| 70 | CH₃ | CH₂N(CH₃)₂ | CH₃ | |
| 71 | CH₃ | CH₂N(CH₃)₂ | H | |
| 72 | CH₃ | CH₂OCH₂–C₆H₅ | CH₃ | 1.5712 |
| 73 | COOCH₂–C₆H₅ | CH₂OCH₂CH₂OCH₃ | CH₃ | 1.5489 |
| 74 | COCH₃ | CH₂OCH₃ | CH₃ | 1.5445 |
| 75 | COCH₃ | CH₂OCH₃ | H | 148–150 |
| 76 | H | CH₂OCH₃ | CH₃ | Unmeasurable |
| 77 | CH₃ | CH₂OCH₃ | CH₃ | Unmeasurable |
| 78 | CH₃ | CH₂OCH₃ | H | |
| 79 | COCH₃ | CH₂OC₂H₅ | CH₃ | 1.5376 |
| 80 | COCH₃ | CH₂OC₂H₅ | H | 142–145 |
| 81 | CH₃ | CH₂OC₂H₅ | CH₃ | |
| 82 | CH₃ | CH₂OC₂H₅ | H | |
| 83 | CH₃ | CH₂OOC₄H₉-t | CH₃ | 1.5256 |
| 84 | H | CO–cyclopropyl | CH₃ | 102–106.5 |
| 85 | H | CO–cyclopropyl | H | 167–169 |
| 86 | H | CO–cyclobutyl | CH₃ | 124–127 |
| 87 | H | CO–cyclobutyl | H | 167–171 |
| 88 | H | CO–cyclopentyl | CH₃ | 91–95 |

TABLE 1-continued

| Comp. No. | R³ | R⁴ | R⁹ | m.p. (°C.) or $n_D^{20}$ |
|---|---|---|---|---|
| 89 | H | CO-cyclopentyl | H | 183–185 |
| 90 | H | CO-cyclohexyl | CH₃ | 125–128 |
| 91 | H | CO-cyclohexyl | H | 94–98 |
| 92 | H | CO-(2-furyl) | CH₃ | 135–136 |
| 93 | H | CO-(2-furyl) | H | 116–120 |
| 94 | H | CO-(2,4-dichlorophenyl) | CH₃ | |
| 95 | H | CO-(2,4-dichlorophenyl) | H | |
| 96 | H | CO-(2-trifluoromethylphenyl) | CH₃ | 161.5–163 |
| 97 | H | CO-(2-trifluoromethylphenyl) | H | 189.5–192 |
| 98 | CH₃ | CO-(2-trifluoromethylphenyl) | CH₃ | 110–113 |

TABLE 1-continued
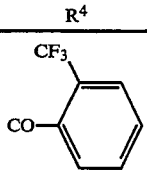
| Comp. No. | R³ | R⁴ | R⁹ | m.p. (°C.) or $n_D^{20}$ |
|---|---|---|---|---|
| 99 | CH₃ | 2-CF₃-C₆H₄-CO- | H | 157–158 |
| 100 | H | 2-Cl-C₆H₄-CO- | CH₃ | 53–55 |
| 101 | H | 2-Cl-C₆H₄-CO- | H | 150–154 |
| 102 | H | 2-CH₃-C₆H₄-CO- | CH₃ | 144–147 |
| 103 | H | 2-CH₃-C₆H₄-CO- | H | 120–125 |
| 104 | CH₃ | 2-CH₃-C₆H₄-CO- | CH₃ | 133.5–135.5 |
| 105 | CH₃ | 2-CH₃-C₆H₄-CO- | H | 106–108 |
| 106 | H | 2-NO₂-C₆H₄-CO- | CH₃ | 198–202 |
| 107 | H | 2-NO₂-C₆H₄-CO- | H | 171–175 |

TABLE 1-continued
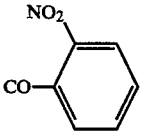
| Comp. No. | R³ | R⁴ | R⁹ | m.p. (°C.) or $n_D^{20}$ |
|---|---|---|---|---|
| 108 | CH₃ | 2-NO₂-C₆H₄-CO- | CH₃ | 158–161 |
| 109 | CH₃ | 2-NO₂-C₆H₄-CO- | H | 173–177 |
| 110 | H | 2-CH₃O-C₆H₄-CO- | CH₃ | 158–160 |
| 111 | H | 2-CH₃O-C₆H₄-CO- | H | 198–201 |
| 112 | CH₃ | 2-CH₃O-C₆H₄-CO- | CH₃ | 138–141 |
| 113 | CH₃ | 2-CH₃O-C₆H₄-CO- | H | 178–180 |
| 114 | H | 3-Cl-C₆H₄-CO- | CH₃ | 152–154 |
| 115 | H | 3-Cl-C₆H₄-CO- | H | 168–171 |
| 116 | H | 3-CH₃-C₆H₄-CO- | CH₃ | 126–129 |

TABLE 1-continued

[Structure: pyridine with N(R³)(R⁴) substituent, COOR⁹, and O-linked pyrimidine with two OCH₃ groups]

| Comp. No. | R³ | R⁴ | R⁹ | m.p. (°C.) or $n_D^{20}$ |
|---|---|---|---|---|
| 117 | H | CO-(3-CH₃-phenyl) | H | 170–171 |
| 118 | H | CO-(4-CF₃-phenyl) | CH₃ | 180–183 |
| 119 | H | CO-(4-CF₃-phenyl) | H | 181–185 |
| 120 | CH₃ | CO-(4-CF₃-phenyl) | CH₃ | 80–83 |
| 121 | H | CO-(4-Cl-phenyl) | CH₃ | 164–166.5 |
| 122 | H | CO-(4-Cl-phenyl) | H | 172–176 |
| 123 | H | CO-(4-CN-phenyl) | CH₃ | |
| 124 | H | CO-(4-CN-phenyl) | H | |
| 125 | H | CO-(4-CH₃-phenyl) | CH₃ | 132–136 |
| 126 | H | CO-(4-CH₃-phenyl) | H | 190–191.5 |
| 127 | H | CO-(4-NO₂-phenyl) | CH₃ | 229–231.5 |

TABLE 1-continued
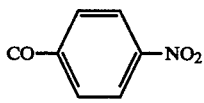
| Comp. No. | $R^3$ | $R^4$ | $R^9$ | m.p. (°C.) or $n_D^{20}$ |
|---|---|---|---|---|
| 128 | H | 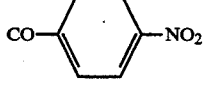 | H | 196–199 |
| 129 | CH$_3$ | 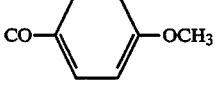 | CH$_3$ | Unmeasurable |
| 130 | CH$_3$ | 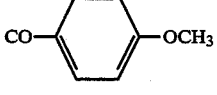 | CH$_3$ | 142–145 |
| 131 | CH$_3$ | 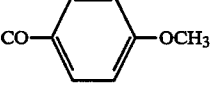 | H | |
| 132 | H | 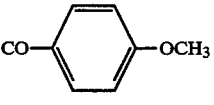 | CH$_3$ | 161–162 |
| 133 | H | 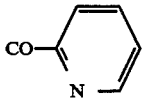 | H | 183–185.5 |
| 134 | CH$_3$ | 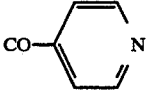 | CH$_3$ | 139–141.5 |
| 135 | CH$_3$ | 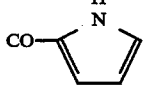 | CH$_3$ | 117–120 |
| 136 | H | 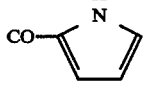 | CH$_3$ | 205–208 |
| 137 | H | 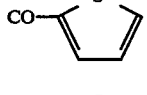 | H | 191–195 |
| 138 | H | 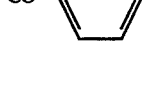 | CH$_3$ | 124–126 |
| 139 | H |  | H | 177–178 |

TABLE 1-continued

[Structure: pyridine with R³R⁴N- at position 6, -COOR⁹ at position 2, and -O-C(=N-CH=C(OCH₃)-CH=C(OCH₃)—) group at position 3]

| Comp. No. | R³ | R⁴ | R⁹ | m.p. (°C.) or $n_D^{20}$ |
|---|---|---|---|---|
| 140 | H | COC(CH₃)=CH₂ | CH₃ | 115–116.5 |
| 141 | H | COC(CH₃)₂COOC₂H₅ | CH₃ | 1.5383 |
| 142 | CH₃ | COC(CH₃)₂COOC₂H₅ | CH₃ | 1.5475 |
| 143 | H | COC₂F₅ | CH₃ | 110–112 |
| 144 | CH₃ | COC₂F₅ | CH₃ | 83–86 |
| 145 | H | COCF₃ | CH₂—C₆H₅ | 86.5–89 |
| 146 | H | COCF₃ | CH₃ | 138–140 |
| 147 | H | COCF₃ | H | 155–160 |
| 148 | CH₃ | COCF₃ | CH₃ | 165–169 |
| 149 | CH₃ | COCF₃ | H | |
| 150 | H | COCH(Br)CH₃ | CH₃ | 108–110 |
| 151 | H | COCH(Br)CH₃ | H | 107–110 |
| 152 | H | COCH=CH—C₆H₅ | CH₃ | 166.5–168 |
| 153 | H | COCH=CH—C₆H₅ | H | 173–176 |
| 154 | H | COCH=CH₂ | CH₃ | 136–137 |
| 155 | CH₃ | COCH=CH₂ | CH₃ | 108–110 |
| 156 | H | COCH=CHCH₃ | CH₃ | 115–117 |
| 157 | H | COCH=CHCH₃ | H | |
| 158 | H | COCH=CHCOOH | CH₃ | 165–169 |
| 159 | H | COCH₂—C₆H₅ | CH₃ | 138–142 |
| 160 | H | COCH₂—C₆H₅ | H | 187–190 |
| 161 | H | COCH₂—C₆H₄(2-Cl) | CH₃ | |
| 162 | H | COCH₂—C₆H₄(2-Cl) | H | |
| 163 | H | COCH₂CH₂Cl | CH₃ | 133–135 |
| 164 | H | COCH₂Cl | CH₃ | 135–140 |
| 165 | H | COCH₂Cl | H | |
| 166 | CH₃ | COCH₂Cl | CH₃ | |

TABLE 1-continued

[Structure: pyridine with R³R⁴N- at position 6, -COOR⁹ at position 2, and -O-C(=N-CH=C(OCH₃)-CH=C-OCH₃ type N,N substituent at position 3]

| Comp. No. | R³ | R⁴ | R⁹ | m.p. (°C.) or n_D^{20} |
|---|---|---|---|---|
| 167 | CH₃ | COCH₂Cl | H | |
| 168 | H | COCH₂CN | CH₃ | |
| 169 | H | COCH₂CN | H | |
| 170 | CH₃ | COCH₂CN | CH₃ | |
| 171 | CH₃ | COCH₂CN | H | |
| 172 | H | COCH₂COOC₂H₅ | CH₃ | 126–128 |
| 173 | H | COCH₂O-C₆H₅ | CH₃ | 133–135 |
| 174 | H | COCH₂O-C₆H₅ | H | 162–166 |
| 175 | H | COCH₂OCH₃ | CH₃ | 120–124 |
| 176 | H | COCH₂OCH₃ | H | 172–174 |
| 177 | H | CON(CH₃)₂ | CH₃ | |
| 178 | H | CON(CH₃)₂ | H | |
| 179 | CH₃ | CON(CH₃)₂ | CH₃ | |
| 180 | CH₃ | CON(CH₃)₂ | H | |
| 181 | H | CONH-C₆H₅ | CH₃ | 236–237 |
| 182 | H | CONH-C₆H₅ | H | 235(D.P) |
| 183 | CH₃ | CONH-C₆H₅ | CH₃ | |
| 184 | CH₃ | CONH-C₆H₅ | H | |
| 185 | CH₃ | CONHC₄H₉ | CH₃ | |
| 186 | H | CONHC₄H₉ | CH₃ | 189–190 |
| 187 | CH₃ | CONHC₄H₉ | CH₃ | |
| 188 | CH₃ | CONHC₄H₉ | H | |
| 189 | H | CONHCH₂-C₆H₅ | CH₃ | |
| 190 | H | CONHCH₂-C₆H₅ | H | |

TABLE 1-continued

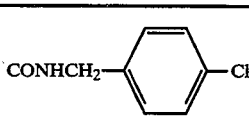

| Comp. No. | R³ | R⁴ | R⁹ | m.p. (°C.) or $n_D^{20}$ |
|---|---|---|---|---|
| 191 | H | CONHCH₂-C₆H₄-Cl | CH₃ | |
| 192 | H | CONHCH₂-C₆H₄-Cl | H | |
| 193 | H | CONHCH₃ | CH₃ | 182–185 |
| 194 | H | CONHCH₃ | H | |
| 195 | CH₃ | CONHCH₃ | CH₃ | |
| 196 | CH₃ | CONHCH₃ | H | |
| 197 | H | CONHC₂H₅ | CH₃ | 200.5–203 |
| 198 | H | CONHC₂H₅ | H | 212–216 |
| 199 | H | CONHC₃H₇ | CH₃ | 200–201 |
| 200 | H | CONHC₃H₇ | H | 214(D.P) |
| 201 | H | CO(CH₂)₄Cl | CH₃ | 90–93 |
| 202 | CH₃ | COOC₄H₉ | CH₃ | |
| 203 | CH₃ | COOC₄H₉ | H | |
| 204 | H | COOC₄H₉-t | CH₃ | 140–142.5 |
| 205 | CH₂OC₂H₅ | COOCH₂-C₆H₅ | CH₃ | 1.5440 |
| 206 | CH₂OC₂H₅ | COOCH₂-C₆H₅ | H | 151–154 |
| 207 | H | COOCH₂-C₆H₅ | CH₃ | 123–125 |
| 208 | H | COOCH₂-C₆H₅ | H | 98–102 |
| 209 | H | COOCH₂C≡CH | CH₃ | |
| 210 | H | COOCH₂C≡CH | H | |
| 211 | CH₃ | COOCH₂C≡CH | CH₃ | |
| 212 | CH₃ | COOCH₂C≡CH | H | |
| 213 | H | COOCH₂CH=CH₂ | CH₃ | 119–121 |
| 214 | H | COOCH₂CH=CH₂ | H | 82–86 |
| 215 | CH₃ | COOCH₂CH=CH₂ | CH₃ | 80–83 |
| 216 | CH₃ | COOCH₂CH=CH₂ | H | 121–124 |
| 217 | H | COOCH₂CH₂OCH₃ | CH₃ | 110–111 |
| 218 | H | COOCH₂CH₂OCH₃ | H | |
| 219 | H | COOCH₂CH₂OCH₃ | H | 79–83 |
| 220 | CH₃ | COOCH₂CH₂OCH₃ | CH₃ | 74–76 |
| 221 | H | COOCH₃ | CH₃ | 146–148.5 |
| 222 | H | COOCH₃ | H | 174–175 |
| 223 | CH₃ | COOCH₃ | CH₃ | 106–108 |
| 224 | CH₃ | COOCH₃ | H | 141–143 |
| 245 | CH₃ | COSCH₂CF₃ | CH₃ | |
| 246 | CH₃ | COSCH₂CF₃ | H | |
| 247 | H | COSCH₂CH=CH₂ | CH₃ | |

TABLE 1-continued

[Structure: pyridine with R³R⁴N- at position 6, -COOR⁹ at position 2, and -O-C(=N-CH(OCH₃)=CH-CH=C(OCH₃)-N-) at position 3]

| Comp. No. | R³ | R⁴ | R⁹ | m.p. (°C.) or $n_D^{20}$ |
|---|---|---|---|---|
| 248 | H | COSCH₂CH=CH₂ | H | |
| 249 | CH₃ | COSCH₂CH=CH₂ | CH₃ | |
| 250 | CH₃ | COSCH₂CH=CH₂ | H | |
| 251 | H | COSC₂H₅ | CH₃ | |
| 252 | H | COSC₂H₅ | H | |
| 253 | CH₃ | COSC₂H₅ | CH₃ | |
| 254 | CH₃ | COSC₂H₅ | H | |
| 255 | H | CSN(CH₃)₂ | CH₃ | 185–186 |
| 256 | H | CSN(CH₃)₂ | H | 165–166 |
| 257 | H | CSNH-C₆H₅ | CH₃ | 236–239 |
| 258 | H | CSNH-C₆H₅ | H | 215(D.P) |
| 259 | H | CSNHC₄H₉ | CH₃ | 200–202 |
| 260 | H | CSNHC₄H₉ | H | 210(D.P) |
| 261 | H | CSNHCH₃ | CH₃ | 185–187 |
| 262 | H | CSNHCH₃ | H | 218(D.P) |
| 263 | H | CSNHC₂H₅ | CH₃ | 203–205 |
| 264 | H | CSNHC₂H₅ | H | 212(D.P) |
| 265 | H | CSNHC₃H₇ | CH₃ | 218–220 |
| 266 | H | CSNHC₃H₇ | H | 215(D.P) |
| 267 | H | OC₄H₉ | CH₃ | |
| 268 | H | OC₄H₉ | H | |
| 269 | CH₃ | OC₄H₉ | CH₃ | |
| 270 | CH₃ | OC₄H₉ | H | |
| 271 | CH₃ | OCH₂-C₆H₅ | CH₃ | |
| 272 | CH₃ | OCH₂-C₆H₅ | H | |
| 273 | H | OCH₃ | CH₃ | |
| 274 | H | OCH₃ | H | |
| 275 | CH₃ | OCH₃ | CH₃ | |
| 276 | CH₃ | OCH₃ | H | 136–139.5 |
| 277 | H | CO-(2-pyridyl) | CH₃ | 146–150 |
| 278 | H | CO-(2-pyridyl) | H | 178–182 |

TABLE 1-continued

[Structure: pyridine with R³R⁴N- group, COOR⁹ group, and O-linked pyrimidine bearing two OCH₃ groups]

| Comp. No. | R³ | R⁴ | R⁹ | m.p. (°C.) or $n_D^{20}$ |
|---|---|---|---|---|
| 279 | H | CO-(3-pyridyl) | CH₃ | 236–239 |
| 280 | H | CO-(3-pyridyl) | H | 201–203 |
| 281 | H | CO-(4-pyridyl) | CH₃ | 85–90 |
| 282 | H | CO-(4-pyridyl) | H | 130–140 |
| 283 | CH₃ | SN(C₄H₉)₂ | CH₃ | |
| 284 | CH₃ | SN(C₄H₉)₂ | H | |
| 285 | CH₃ | SN(CH₃)COOC₄H₉ | CH₃ | |
| 286 | CH₃ | SN(CH₃)COOC₄H₉ | H | |
| 287 | CH₃ | S-morpholino | CH₃ | |
| 288 | CH₃ | S-morpholino | H | |
| 289 | H | SO₂-phenyl | CH₃ | 72–75 |
| 290 | H | SO₂-phenyl | H | 88–91 |
| 291 | SO₂-phenyl | SO₂-phenyl | CH₃ | 147.5–150.5 |
| 292 | H | SO₂-(2-chlorophenyl) | CH₃ | |

TABLE 1-continued
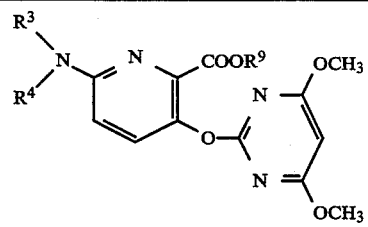
| Comp. No. | R³ | R⁴ | R⁹ | m.p. (°C.) or $n_D^{20}$ |
|---|---|---|---|---|
| 293 | H | 2-Cl-C₆H₄-SO₂- | H | |
| 294 | H | 2-COOCH₃-C₆H₄-SO₂- | CH₃ | |
| 295 | H | 2-COOCH₃-C₆H₄-SO₂- | H | |
| 296 | CH₃ | SO₂CF₃ | CH₃ | |
| 297 | CH₃ | SO₂CF₃ | H | |
| 298 | H | 2-COOCH₃-C₆H₄-CH₂-SO₂- | CH₃ | |
| 299 | H | 2-COOCH₃-C₆H₄-CH₂-SO₂- | H | |
| 300 | H | SO₂CH₃ | CH₃ | 144–146 |
| 301 | H | SO₂CH₃ | H | 208–211 |
| 302 | CH₃ | SO₂CH₃ | CH₃ | 125–127.5 |
| 303 | CH₃ | SO₂CH₃ | H | 145–147 |
TABLE 2
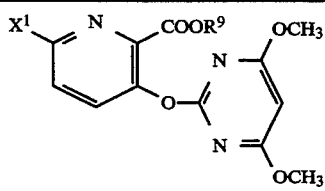
| Comp. No. | X¹ | R⁹ | m.p. (°C.) or $n_D^{20}$ |
|---|---|---|---|
| 304 | maleimido (N-) | CH₃ | 164–168 |
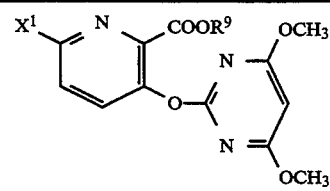
| Comp. No. | X¹ | R⁹ | m.p. (°C.) or $n_D^{20}$ |
|---|---|---|---|
| 305 | maleimido (N-) | H | |

TABLE 2-continued

[Structure: X¹-substituted pyridine with COOR⁹ group and O-linked pyrimidine bearing two OCH₃ groups]

| Comp. No. | X¹ | R⁹ | m.p. (°C.) or $n_D^{20}$ |
|---|---|---|---|
| 306 | succinimido (2,5-dioxopyrrolidin-1-yl) | CH₃ | |
| 307 | succinimido (2,5-dioxopyrrolidin-1-yl) | H | |
| 308 | phthalimido | CH₃ | |
| 309 | phthalimido | H | |
| 310 | 2-oxopyrrolidin-1-yl | CH₃ | 194–198 |
| 311 | 2-oxopyrrolidin-1-yl | H | 189–190 |
| 312 | 2-oxo-1,3-oxazolidin-3-yl | CH₃ | 178–182 |
| 313 | 2-oxo-1,3-oxazolidin-3-yl | H | 169–173 |
| 314 | pyrrol-1-yl | CH₃ | |
| 315 | pyrrol-1-yl | H | |
| 316 | morpholin-4-yl | H | 181–183 |
| 317 | pyrrolidin-1-yl | CH₃ | 151–153 |
| 318 | pyrrolidin-1-yl | H | 179–183 |
| 319 | NCS | CH₃ | 116–117 |
| 320 | N=C(NH₂)S CH₃ | CH₃ | 109–112 |
| 321 | N=CH—N(CH₃)₂ | CH₃ | 133–137 |
| 322 | N=C(CH₃)₂ | CH₃ | |
| 323 | N=C(CH₃)₂ | H | |
| 324 | N=C(CH₃)C₆H₅ | CH₃ | |
| 325 | N=C(CH₃)C₆H₅ | H | |
| 326 | N=CHC₆H₅ | CH₃ | |
| 327 | N=CHC₆H₅ | H | |
| 328 | N=CHC₄H₉ | CH₃ | |
| 329 | N=CHC₄H₉ | H | |
| 330 | N=CHCH₂C₆H₅ | CH₃ | |
| 331 | N=CHCH₂C₆H₅ | H | |
| 332 | N=CHCH₃ | CH₃ | |
| 333 | N=CHCH₃ | H | |
| 334 | N₃ | CH₃ | 125–128 |
| 335 | N₃ | H | 112–115 |

TABLE 3

Structure: pyridine with $R^3R^4N-$ at position 2, W substituent, and $-O-$ linked to 4,6-dimethoxypyrimidin-2-yl

| Comp. No. | $R^3$ | $R^4$ | W | m.p. (°C.) or $n_D^{20}$ |
|---|---|---|---|---|
| 336 | H | H | $COON(C_2H_5)_2$ | 116–118.5 |
| 337 | H | H | $COON=C(CH_3)_2$ | 210–214 |
| 338 | H | H | $COON=C(CH_3)C_2H_5$ | 178–181 |
| 339 | H | H | COON=cyclopentyl | 198–201 |
| 340 | H | H | COO-phenyl | 141–144 |
| 341 | H | H | COO-(2-Cl-phenyl) | 153–156 |
| 342 | H | H | COO-(2-CH$_3$-phenyl) | 153–157 |
| 343 | H | H | COS-phenyl | 170–171.5 |
| 344 | H | H | $COSC_2H_5$ | 115–118 |
| 345 | H | $CH_3$ | $COSC_3H_7$-i | |
| 346 | $CH_3$ | $CH_3$ | CO-N(imidazolyl) | 118–123 |
| 347 | $CH_3$ | $CH_3$ | $CON(Na)SO_2CH_3$ | 135–158 |
| 348 | $CH_3$ | $CH_3$ | $CON(CH_2OC_2H_5)SO_2CH_3$ | 111–113 |
| 349 | $CH_3$ | $CH_3$ | $CON(CH_3)OCH_3$ | 157–161 |
| 350 | $CH_3$ | $CH_3$ | $CONHOCH_2$-phenyl | 138–142 |
| 351 | $CH_3$ | $CH_3$ | $CONHSO_2CH_3$ | 200–202 |
| 352 | $CH_3$ | $CH_3$ | $COOCH_2OCH_2$-phenyl | 1.5828 |
| 353 | $CH_3$ | $CH_3$ | $COON=C(CH_3)_2$ | 1.5637 |
| 354 | $CH_3$ | $CH_3$ | $COON=C(C_3H_7)_2$ | 1.5489 |
| 355 | $CH_3$ | $CH_3$ | $COSC_5H_{11}$ | 126–128 |

TABLE 3-continued

| Comp. No. | $R^3$ | $R^4$ | W | m.p. (°C.) or $n_D^{20}$ |
|---|---|---|---|---|
| 356 | $CH_3$ | $CH_3$ | $COSC_3H_7$ | 134–136 |

TABLE 4

Structure: pyridine with $R^3R^4N-$ at 2-position, $COOR^{14}$ group, Y linker to 4,6-dimethoxypyrimidin-2-yl

| Comp. No. | $R^3$ | $R^4$ | Y | $R^{14}$ | m.p. (°C.) or $n_D^{20}$ |
|---|---|---|---|---|---|
| 357 | H | H | —CH(CN)— | H | |
| 358 | H | H | —CO— | H | |
| 359 | H | H | —CH$_2$— | H | |
| 360 | H | $CH_3$ | —CH(CN)— | H | |
| 361 | H | $CH_3$ | —CO— | H | |
| 362 | H | $CH_3$ | —CH$_2$— | H | |
| 363 | $CH_3$ | $CH_3$ | —CH(CN)— | $CH_3$ | |
| 364 | $CH_3$ | $CH_3$ | —CH(CN)— | H | |
| 365 | $CH_3$ | $CH_3$ | —CO— | $CH_3$ | |
| 366 | $CH_3$ | $CH_3$ | —CO— | H | |
| 367 | $CH_3$ | $CH_3$ | —CH$_2$— | $CH_3$ | |
| 368 | $CH_3$ | $CH_3$ | —CH$_2$— | H | |

TABLE 5

Structure: pyridine with $(CH_3)_2N-$ at 2-position, Z substituent on ring nitrogen, $COOCH_3$, and $-O-$ linked to 4,6-dimethoxypyrimidin-2-yl

| Comp. No. | Z | m.p. (°C.) or $n_D^{20}$ |
|---|---|---|
| 369 | $CH_3.I$ | 167–169 |
| 370 | $COCH_3.Cl$ | |
| 371 | $SO_2CH_3.Cl$ | |

As a method for producing compounds of the present invention, the following processes A to K may, for example, be mentioned, but the method is not restricted to such specific processes.

Process A

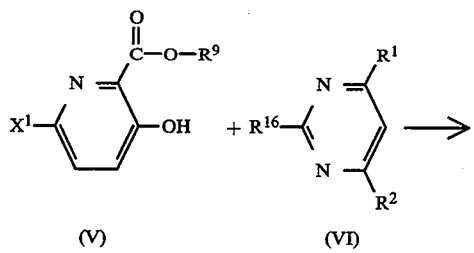

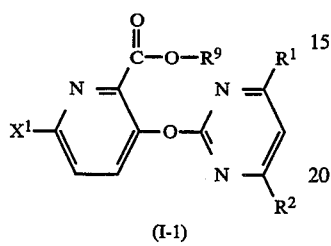

In the above formulas, $R^1$, $R^2$, $R^9$ and $X^1$ are as defined above, and $R^{16}$ is a halogen atom, an alkylsulfonyl group or a benzylsulfonyl group.

Namely, the compound of the formula (I-1) of the present invention can be produced by reacting the compound of the formula (V) and the pyrimidine derivative of the formula (VI) in the presence of a base, preferably in an inert solvent, within a temperature range of from 0° C. to the boiling point of the solvent for from a few minutes to dozens of hours.

The solvent may be a hydrocarbon solvent such as benzene or toluene, a halogenated hydrocarbon solvent such as dichloromethane or chloroform, an ether solvent such as tetrahydrofuran or 1,4-dioxane, a ketone solvent such as acetone or methyl ethyl ketone (MEK), an ester solvent such as methyl acetate or ethyl acetate, an aprotic polar solvent such as N,N-dimethylformamide (DMF) or N,N-dimethylacetamide (DMAc), or acetonitrile. However, the solvent is not limited to such specific examples.

The base may, for example, be an alkali metal such as metal sodium or metal potassium, an alkali metal hydride or alkaline earth metal hydride such as sodium hydride, potassium hydride or calcium hydride, a carbonate such as sodium carbonate, potassium carbonate or calcium carbonate, or a metal hydroxide such as sodium hydroxide, potassium hydroxide or calcium hydroxide. However, the base is not limited to such specific examples. Such a base can be used in a suitable combination with the solvent.

Process B

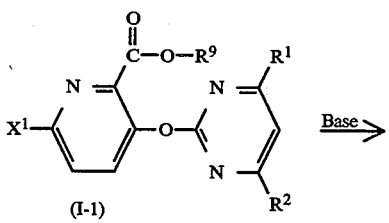

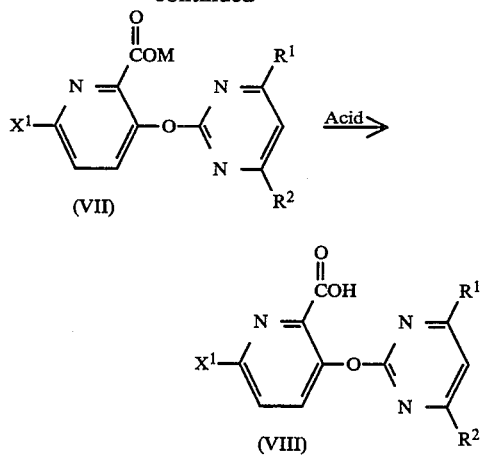

In the above formulas, $R^1$, $R^2$, $R^9$ and $X^1$ are as defined above, and M is an alkali metal, an alkaline earth metal or an organic amine cation.

Namely, among compounds of the present invention, the compound of the formula (VII) can be obtained by reacting the formula (I-1) in the presence of a base in a polar solvent or water or in a solvent mixture of a polar solvent and water within a temperature range of from room temperature to the boiling point of the solvent for from a few hours to dozens of hours. The product is then precipitated with an acid to obtain a compound of the formula (VIII).

The solvent may, for example, be an alcohol solvent such as methanol or ethanol, an ether polar solvent such as 1,4-dioxane or tetrahydrofuran (THF), an aprotic polar solvent such as DMF, DMAc or dimethylsulfoxide, or acetonitrile. However, the solvent is not limited to such specific examples. The base may, for example, be a carbonate such as sodium carbonate, potassium carbonate or calcium carbonate, or a metal hydroxide such as sodium hydroxide, potassium hydroxide or calcium hydroxide.

Process C

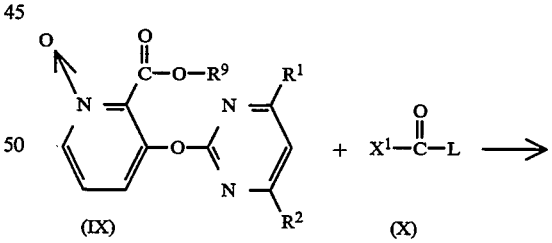

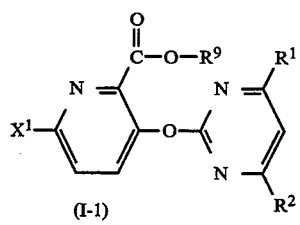

In the above formulas, $R^1$, $R^2$, $R^9$ and $X^1$ are as defined above, and L is a leaving group.

Namely, the compound of the formula (IX) and the compound of the formula (X) are reacted in an inert solvent within a temperature range of from 0° C. to the boiling point of the solvent for from a few minutes to dozens of hours to obtain the compound of the formula (I-1). Here, the solvent may, for example, be a hydrocarbon solvent such as toluene, benzene or xylene, a halogenated hydrocarbon solvent such as dichloromethane or chloroform, an ether solvent such as ethyl ether, isopropyl ether, tetrahydrofuran or 1,4-dioxane, an aprotic polar solvent such as DMF, DMAc or dimethylsulfoxide, an ester such as ethyl acetate, acetonitrile or chloroform. Preferred is acetonitrile or tetrahydrofuran. The solvent is used in an amount of from 0.1 to 10 l, preferably from 1.0 to 5.0 l, per mol of the compound of the formula (IX). As a preferred condition, refluxing in acetonitrile may be mentioned. The compound of the formula (X) may be used in an equal amount or more to the compound of the formula (IX).

In this reaction, the reaction may proceed without addition of a base. However, it is preferred to add a base. The base may, for example, be an alkali metal or an alkaline earth metal, particularly a carbonate, a hydrogencarbonate, an acetate, an alkoxide, a hydroxide or an oxide of sodium, potassium, magnesium or calcium. Further, an organic base such as pyridine or a tertiary amine such as triethylamine or N,N-diisopropylethylamine may be used. Preferred is N,N-diisopropylethylamine. The amount of the base is preferably at least an equimolar amount to the compound of the formula (X), but it is not particularly limited. The leaving group may, for example, be a halogen atom such as a chlorine atom, an alkoxy group, or 1-imidazolyl group. Preferred is a chlorine atom. When the leaving group is a chlorine atom, the reactivity of the compound of the formula (X) can be increased by adding potassium iodide or sodium iodide in an amount of from a catalytic amount to an equimolar amount to the compound of the formula (X).

Process D

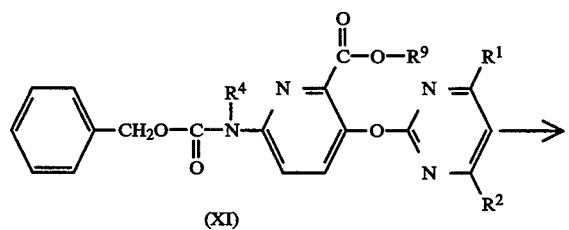

(XI)

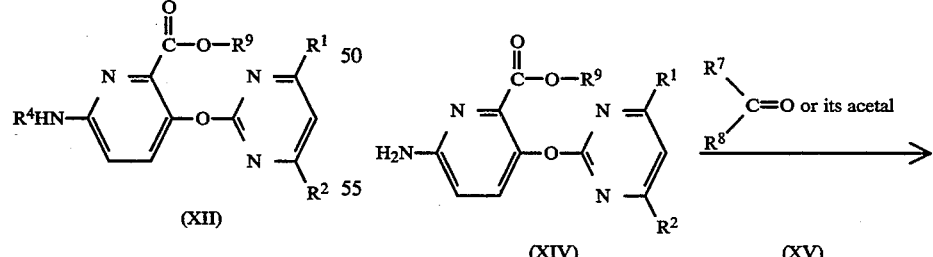

(XII)

In the above formulas, $R^1$, $R^2$, $R^4$ and $R^9$ are as defined above.

Namely, the compound of the formula (XII) can be produced by catalytic hydrogenation reaction of a compound of the formula (XI) in the presence of a catalyst in an inert solvent within a temperature range of from 0° C. to the boiling point of the solvent for from a few minutes to dozens of hours. The solvent may be the same as in Process A (except a halogenated hydrocarbon solvent), and the catalyst may, for example, be a reducing metal catalyst such as palladium carbon or Raney nickel, but the catalyst is not particularly limited. Further, depending upon the reaction, the reaction may be accelerated by an addition of a small amount of an acid such as acetic acid, sulfuric acid or a perchloric acid. As a preferred embodiment, a method may be mentioned in which the hydrogenation is conducted in a methanol solvent at room temperature in the presence of palladium carbon as a catalyst.

The compound of the formula (XI) of the present invention can be produced also by Process C as described above.

Process E

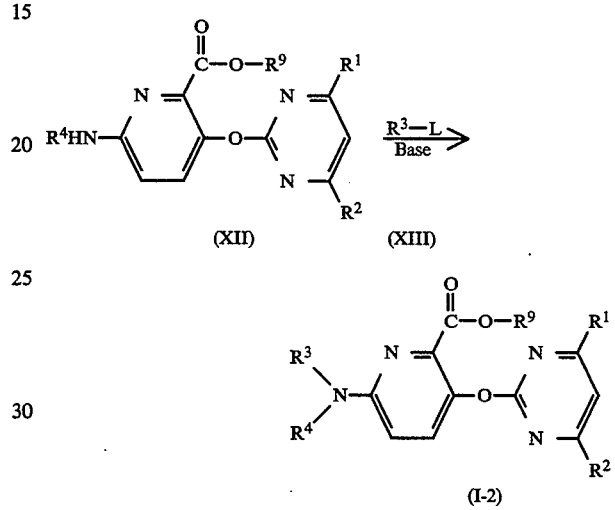

In the above formulas, $R^1$, $R^2$, $R^3$, $R^4$ and $R^9$ are as defined above, and L is a leaving group.

Namely, the compound of the formula (I-2) of the present invention can be prepared by reacting the compound of the formula (XII) and the compound of the formula (XIII) in the presence of a base in an inert solvent within a temperature range of from 0° C. to the boiling point of the solvent for from a few minutes to dozens of hours.

The solvent and the base may be the same as in Process A, but they are not particularly limited.

Process F

In the above formulas, $R^1$, $R^2$, $R^7$, $R^8$ and $R^9$ are as defined above.

Namely, the compound of the formula (XVI) of the present invention can be produced by reacting the compound of the formula (XIV) and the compound of the formula (XV) within a temperature range of from 0° C. to the boiling point of the compound of the formula (XV) for from a few minutes to dozens of hours. This reaction may be conducted by an addition of an inert solvent, and the solvent for this purpose may be the same as in Process A but is not particularly limited. Further, the reaction may be accelerated, for example, by an addition of a small amount of a Lewis acid as an acid catalyst, by dehydration operation by means of a Deanstark tube or by dehydration operation by means of a molecular sieve. The combination of such conditions is not particularly limited. However, as a preferred embodiment, a reaction under reflux in a methanol solvent may be mentioned.

Process G

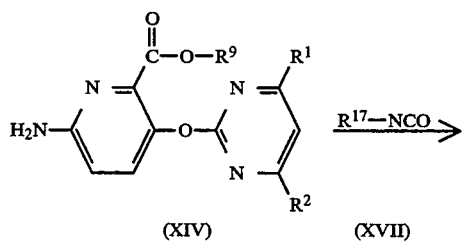

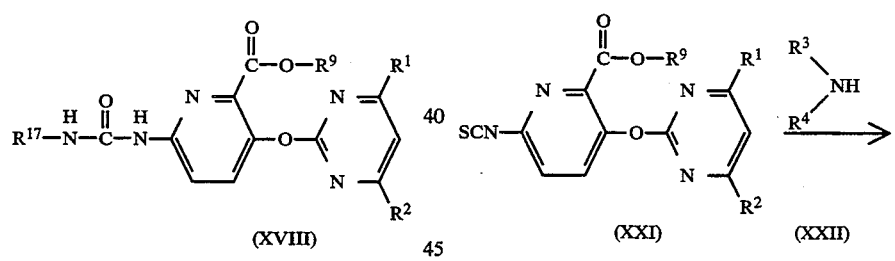

In the above formulas, $R^1$, $R^2$ and $R^9$ are as defined above, and $R^{17}$ is an alkyl group, a phenyl group or a benzyl group.

Namely, the compound of the formula (XVIII) can be produced by reacting the compound of the formula (XIV) and the compound of the formula (XVII) in an inert solvent within a temperature range of from 0° C. to the boiling point of the solvent for from a few minutes to dozens of hours.

The solvent to be used here may be the same as in Process A. For this reaction, a base may be used as a catalyst. Such a base may be the same as in Process A. Further, when the compound of the formula (XVII) is liquid, the reaction can be conducted without using the inert solvent. As a preferred embodiment, a reaction may be mentioned in which an organic amine such as triethylamine is added in MEK or a halogenated hydrocarbon solvent. However, the reaction is not particularly limited to such an embodiment.

Process H

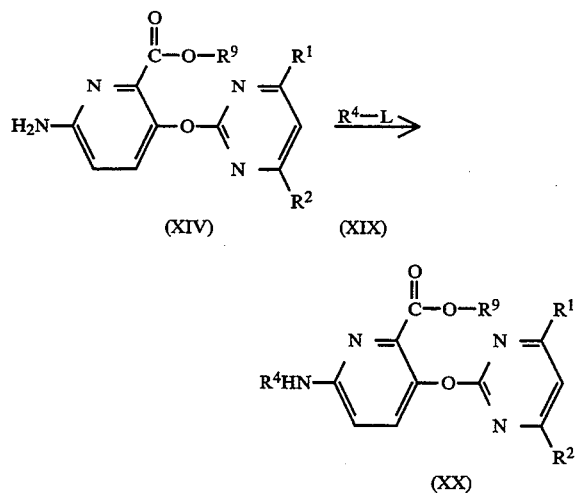

In the above formulas, $R^1$, $R^2$, $R^3$, $R^9$ and L are as defined above.

Namely, the compound of the formula (XX) of the present invention can be produced by reacting the compound of the formula (XIV) and the compound of the formula (XIX) in the presence of a base within a temperature range of from 0° C. to the boiling point of the solvent for a few minutes to dozens of hours.

The solvent and the base to be used here may be the same as in Process A.

Process I

In the above formulas, $R^1$, $R^2$, $R^3$, $R^4$ and $R^9$ are as defined above.

Namely, the compound of the formula (XXIII) of the present invention can be prepared by reacting the compound of the formula (XXI) and the compound of the formula (XXII) in an inert solvent within a temperature range of from 0° C. to the boiling point of the solvent from a few minutes to dozens of hours.

The solvent to be used here, may be the same as in Process A. In this reaction, a base may be used as a catalyst, and such a base may be the same as in Process A. Further, when the compound of the formula (XXIII) is liquid, the reaction can be conducted without using the inert solvent. As a preferred embodiment, a reaction in a halogenated hydrocarbon solvent may be mentioned, but the reaction is not particularly limited.

Synthesis of the compound of the formula (XXII) is described in Preparation Example 19.

Process J

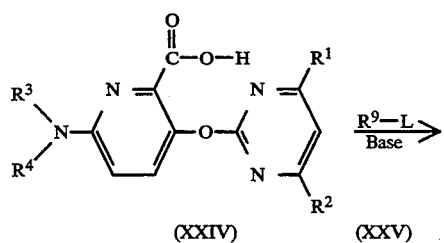

(XXIV)    (XXV)

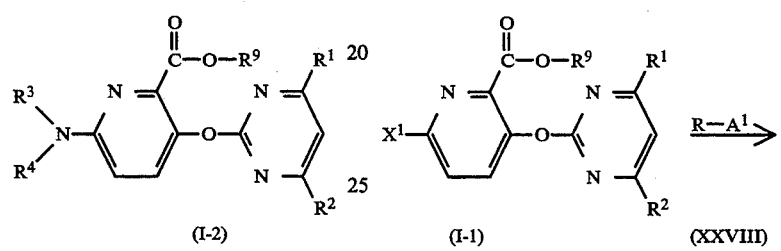

(I-2)    (I-1)    (XXVIII)

In the above formulas, $R^1$, $R^2$, $R^3$, $R^4$, $R^9$ and L are as defined above.

Namely, the compound of the formula (I-2) of the present invention can be produced by reacting the compound of the formula (XXIV) and the compound of the formula (XXV) in the presence of a base in an inert solvent within a temperature range of from 0° C. to the boiling point of the solvent for from a few minutes to dozens of hours.

The solvent and the base to be used here may be the same as in Process A.

Process K

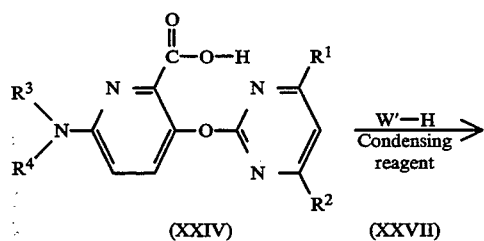

(XXIV)    (XXVII)

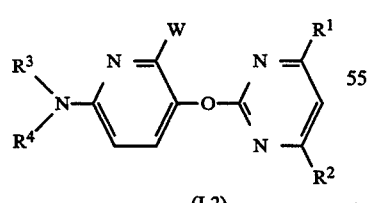

(I-2)

In the above formulas, $W^1$ is $R^{10}O$, $R^{11}S$ or $R^{12}R^{13}N$, and $R^1$, $R^2$, $R^3$, $R^4$, $R^{10}$, $R^{11}$, $R^{12}$, $R^{13}$ and W are as defined above.

Namely, the compound of the formula (I-2) of the present invention can be produced by reacting the compound of the formula (XXVI) and the compound of the formula (XXVII) in the presence of a condensing reagent in a inert solvent within a temperature range of from 0° C. to the boiling point of the solvent for from a few minutes to dozens of hours.

The solvent to be used here may be the same as in Process A. The condensing reagent may be a carbonyldiimidazole or a combination thereof with a base, a combination of triphenylphosphine and diethylazodicarboxylate, diethylcyanophosphate, or an organic base. For the above two cases, the solvent is preferably THF or DMF. The combination of the condensing reagent and the solvent is not particularly limited.

Process L

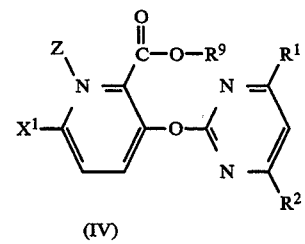

(IV)

In the above formulas, $R^1$, $R^2$, $R^9$, $X^1$ and Z are as defined above and R is an alkyl group, an acyl group or an alkylsulfonyl group and $A^1$ is a halogen atom.

Namely, the compound of the formula (IV) of the present invention can be produced by reacting the compound of the formula (I-1) and the compound of the formula (XXVIII) within a temperature range of from 0° C. to the boiling point of the solvent for from a few minutes to dozens of hours.

The solvent and the base to be used here may be the same as in Process A.

Process M

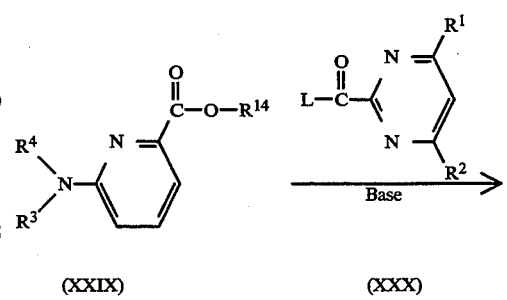

(XXIX)    (XXX)

-continued

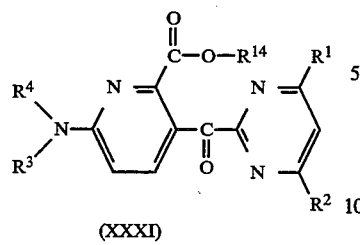

(XXXI)

In the above formulas, $R^1$, $R^2$, $R^3$, $R^4$, $R^{14}$ and L are as defined above.

Namely, the compound of the formula (XXXI) can be produced by reacting the compound of the formula (XXIX) and the compound of the formula (XXX) in an inert solvent in the presence of a base.

The base and the solvent to be used here are the same as in Process A, and they are not particularly limited. Preferably a combination of an organic metal such as n-butyl lithium and a THF solvent, may be mentioned.

Process N

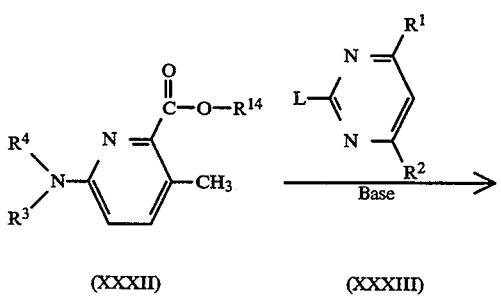

(XXXII)         (XXXIII)

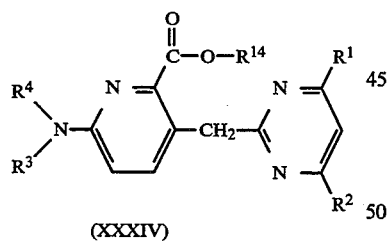

(XXXIV)

In the above formulas, $R^1$, $R^2$, $R^3$, $R^4$, $R^{14}$ and L are as defined above.

Namely, the compound of the formula (XXXIV) of the present invention can be produced by reacting the compound of the formula (XXXII) and the compound of the formula (XXXIII) in an inert solvent in the presence of a base.

The base and the solvent to be used here may be the same as in Process A, and they are not particularly limited. Preferably, a combination of an organic metal such as n-butyl lithium and a THF solvent, may be mentioned.

Process O

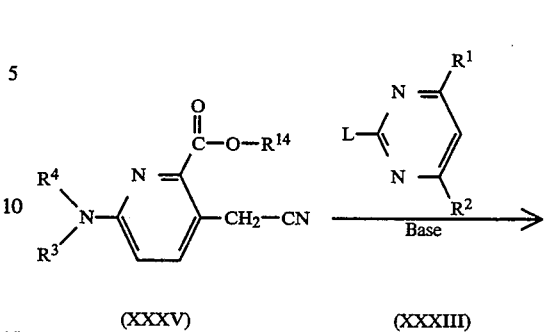

(XXXV)         (XXXIII)

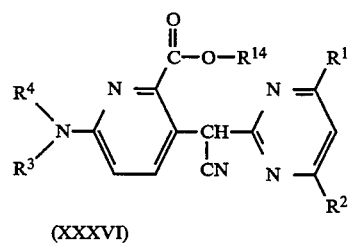

(XXXVI)

In the above formulas, $R^1$, $R^2$, $R^3$, $R^4$, $R^{14}$ and L are as defined above.

Namely, the compound of the formula (XXXVI) can be produced by reacting the compound of the formula (XXXV) and the compound of the formula (XXXIII) in an inert solvent within a temperature range of from −50° C. to the boiling point of the solvent in the presence of a base.

The base and the solvent to be used here may be the same as in Process A, and they are not particularly limited. Preferably, a combination of using a base such as sodium hydride or tert-butoxypotassium in an aprotic polar solvent such as DMF or dimethylsulfoxide, or a combination of an alkali metal such as n-butyl lithium and a THF solvent may be mentioned.

Now, the processes as well as the formulations and use of the present invention will be described in more detail with Preparation Examples. However, it should be understood that the present invention is by no means restricted to such specific Examples.

EXAMPLE 1

Preparation of methyl 3-[(4,6-dimethoxypyrimidin-2-yl)oxy]-6-(1-pyrrolidinyl)picolinate (Compound No. 317)

1.55 g (7 mmol) of methyl 3-hydroxy-6-(1-pyrrolidinyl)picolinate, 1.83 g (8.4 mmol) of 4,6-dimethoxy-2-methylsulfonylpyrimidine and 0.96 g (7 mmol) of potassium carbonate were added to 50 ml of DMF and reacted at 100° C. for 3 hours. After completion of the reaction, the reaction product was poured into ice water, extracted with ethyl acetate, washed with a saturated sodium chloride aqueous solution and dried over magnesium sulfate. The solvent was distilled off, and the residue was crystallized from diisopropyl ether to obtain the desired product.

Amount: 2.11 g (yield: 84%), melting point: 151°–153° C.

EXAMPLE 2

Preparation of 3-[(4,6-dimethoxypyridmidin-2-yl)oxy]-6-(N-methyl-N-cyclohexylamino)picolinic acid (Compound No. 21)

6.2 g (15 mmol) of methyl 3-[(4,6-dimethoxypyrimidin-2-yl)oxy]-6-(N-methyl-N-cyclohexylamino)picolinate was dissolved in 60 ml of methanol. To this solution, 1.1 g (20 mmol) of potassium hydroxide dissolved in 30 ml of water, was added, and the mixture was reacted at 50° C. for one hour. The reaction solution was concentrated and then adjusted to pH7 by an addition of a saturated citric acid aqueous solution. Then, it was extracted with chloroform and then dried and concentrated to obtain crude crystals, which were recrystallized from ethanol to obtain the desired product.

Amount: 3.6 g (yield: 60.0%), melting point: 144°–147° C.

EXAMPLE 3

Preparation of 3-[(4,6-dimethoxypyrimidin-2-yl)oxy]-6-(1-pyrrolidinyl)picolinic acid (Compound No. 318)

1.44 g (4 mmol) of methyl 3-[(4,6-dimethoxypyrimidin-2-yl)oxy]-6-(1-pyrrolidinyl)picolinate and 0.67 g (12 mmol) of potassium hydroxide were added to 30 ml of methanol, 30 ml of 1,2-dimethoxyethane and 10 ml of water, and the mixture was reacted at 40° C. for 4 hours. The solvent was distilled off, and water was added to the residue. The mixture was acidified (pH=4) by 10% hydrochloric acid, then extracted with chloroform and ethyl acetate, dried and concentrated, and then crystallized from diisopropyl ether to obtain the desired product.

Amount: 1.29 g (yield: 94%), melting point: 179°–183° C.

EXAMPLE 4

Preparation of methyl 3-[(4,6-dimethoxypyrimidin-2-yl)oxy]-6-(N-methyl-N-cyclohexylamino)picolinate (Compound No. 20)

11.0 g (36 mmol) of methyl 3-[(4,6-dimethoxypyrimidin-2-yl)oxy]picolinate N-oxide, 9.5 g (54 mmol) of N-methyl-N-cyclohexylcarbamoyl chloride, 10.5 g (70 mmol) of sodium iodide and 9.0 g (70 mmol) of diisopropylethylamine were added to 150 ml of acetonitrile and reacted at a temperature of from 60° to 70° C. for one hour. Water was added to the reaction solution, and the organic layer was extracted with ethyl acetate, dried and concentrated. The obtained oily product was purified by silica gel column chromatography (ethyl acetate-hexane) to obtain the desired product.

Amount: 7.2 g (yield: 50%), melting point: 116°–117.5° C.

EXAMPLE 5

Preparation of methyl 3-[(4,6-dimethoxypyrimidin-2-yl)oxy]-6-(N-methyl-N-benzylamino)picolinate (Compound No. 26)

20 g (77.1 mmol) of methyl 3-[(4,6-dimethoxypyrimidin-2-yl)oxy]picolinate N-oxide, 15 g (116 mmol) of diisopropylethylamine and 46.2 g (308.2 mmol) of sodium iodide were suspended in 200 ml of acetonitrile and stirred at room temperature for 15 minutes. To this mixture, 21.2 g (115.4 mmol) of N-methyl-N-benzylcarbamoyl chloride dissolved in 20 ml of acetonitrile was added at room temperature. The mixture was refluxed. Foaming started at a temperature slightly lower than the boiling point, and such foaming terminated in about 30 minutes. The reaction was continued for further 10 minutes. The reaction solution was poured into water and extracted with ethyl acetate. The extract was washed with water, dried, concentrated and then purified by silica gel column chromatography to obtain the desired product.

Amount: 9.0 g (yield: 32%), melting point: 73°–75° C.

EXAMPLE 6

Preparation of methyl 3-[(4,6-dimethoxypyrimidin-2-yl)oxy]-6-[2-(phenoxy)ethylamino]picolinate (Compound No. 64)

1.12 g (2 mmol) of methyl 3-[(4,6-dimethoxypyrimidin-2-yl)oxy]-6-[N-(2-phenoxy)ethyl-N-benzyloxycarbonylamino]picolinate was catalytically reduced in 30 ml of methanol in the presence of 1 g of palladium carbon (10%). The catalyst was filtered off, and the filtrate was distilled under reduced pressure at a low temperature of not higher than 40° C., and the residual oily product was purified by column chromatography to obtain the desired product as colorless transparent oily product.

Amount: 0.6 g (yield: 70.4%), refractive index: 1.5682

EXAMPLE 7

Preparation of methyl 3-[(4,6-dimethoxypyrimidin-2-yl)oxy]-6-(N-methoxymethyl-N-methyl)aminopicolinate (Compound No. 77)

2.1 g (6.6 mmol) of methyl 3-[(4,6-dimethoxypyrimidin-2-yl)oxy]-6-methylaminopicolinate and 1.30 g (10.0 mmol) of N,N-diisopropylethylamine were added to 20 ml of dichloromethane, and 0.80 g (10.0 mmol) of methoxymethyl chloride was added thereto at room temperature. The mixture was left to stand overnight, and then dichloromethane was distilled off under reduced pressure. The residue was purified by silica gel column chromatography to obtain the desired product.

Amount: 0.30 g (yield: 12.5%)

EXAMPLE 8

Preparation of methyl 3-[(4,6-dimethoxypyrimidin-2-yl)oxy]-6-(N,N-dimethylaminomethyleneamino)picolinate (Compound No. 321)

2.0 g (6.5 mmol) of methyl 6-amino-3-[(4,6-dimethoxypyrimidin-2-yl)oxy]picolinate and 1.5 g (10 mmol) of N,N-dimethylformamide diethylacetal were added to 20 ml of ethanol, and the mixture was stirred and refluxed for two hours. After completion of the reaction, the solvent was distilled off under reduced pressure. The residue was purified by column chromatography to obtain the desired product as colorless transparent prism crystals.

Amount: 1.5 g (yield: 65.2%), melting point: 133°–137° C.

EXAMPLE 9

Preparation of methyl 3-[(4,6-dimethoxypyrimidin-2-yl)oxy]-6-(N-phenylcarbamoylamino)picolinate (Compound No. 181)

2 g (6.5 mmol) of methyl 6-amino-3-[(4,6-dimethoxypyrimidin-2-yl)oxy]picolinate, 0.77 g (7.15 mmol) of phenyl isocyanate and a catalytic amount of crystals of 1,4-diazabicyclo-[2.2.2]-octane were added to 50 ml of MEK, and the mixture was stirred and refluxed for 4 hours. After completion of the reaction, the product was filtered and washed with MEK to obtain the desired product as colorless transparent crystals.

Amount: 1.97 g (yield: 71.1%), melting point: 236°–237° C.

EXAMPLE 10

Preparation of methyl 3-[(4,6-dimethoxypyrimidin-2-yl)oxy]-6-[N-(1,1,1-trifluoroacetyl)amino]picolinate (Compound No. 146)

5.8 g (27.4 mmol) of methyl 6-amino-3-[(4,6-dimethoxypyrimidin-2-yl)oxy]picolinate, 7.6 g (24.9 mmol) of trifluoroacetic anhydride and 2.6 g (32.4 mmol) of pyridine were added to 60 ml of MEK, and the mixture was stirred at room temperature for one hour. After completion of the reaction, the reaction mixture was poured into a dilute alkaline aqueous solution, then extracted with ethyl acetate. The extract was washed with water, dried and concentrated. Then, obtained crude crystals were recrystallized from ethanol to obtain the desired product as colorless transparent crystals.

Amount: 7.7 g (yield: 77%), melting point: 138°–140° C.

EXAMPLE 11

Preparation of methyl 3-[(4,6-dimethoxypyrimidin-2-yl)oxy]-6-(methylsulfonylamino)picolinate (Compound No. 300)

3.1 g (10 mmol) of methyl 3-[(4,6-dimethoxypyrimidin-2-yl)oxy]-6-aminopicolinate, 2.4 g (21 mmol) of methanesulfonyl chloride and 1.5 g (11 mmol) of potassium carbonate were added to 10 ml of MEK, and the mixture was stirred and refluxed for 12 hours. After completion of the reaction, the solvent was distilled off under reduced pressure. The residual oily product was purified by column chromatography and then crystallized from diisopropyl ether to obtain the desired product as a slightly yellow powder.

Amount: 0.75 g (yield: 19.7%), melting point: 144°–146° C.

EXAMPLE 12

Preparation of methyl 6-(2-butenylamino)-3-[(4,6-dimethoxypyrimidin-2-yl)oxy]picolinate (Compound No. 56)

3.0 g (9.8 mmol) of methyl 6-amino-3-[(4,6-dimethoxypyrimidin-2-yl)oxy]picolinate, 1.5 g (10.8 mmol) of 2-butenyl bromide and 1.6 g (11.8 mmol) of potassium carbonate were added to 10 ml of DMF, and the mixture was stirred at 100° C. for one hour. After completion of the reaction, the reaction mixture was poured into water, then extracted with ethyl acetate, dried and concentrated. Then, the obtained residue was purified by column chromatography and crystallized to obtain a solid, which was washed with diisopropyl ether to obtain the desired product as colorless prism crystals.

Amount: 1.28 g (yield: 36.6%), melting point: 82°–85° C.

EXAMPLE 13

Preparation of methyl 3-[(4,6-dimethoxypyrimidin-2-yl)oxy]-6-(N-n-propylthiocarbamoylamino)picolinate (Compound No. 265)

2 g (5.7 mmol) of methyl 3-[(4,6-dimethoxypyrimidin-2-yl)oxy]-6-(isothiocyanate)picolinate and 0.4 g (6.8 mmol) of n-propylamine were added to 50 ml of dichloromethane, and the mixture was stirred at room temperature for 12 hours. After completion of the reaction, the product was filtered and washed with dichloromethane to obtain the desired product as colorless transparent crystals.

Amount: 2.2 g (yield: 94%), melting point: 218°–220° C.

EXAMPLE 14

Preparation of isopropylideneamino 6-amino-3-[(4,6-dimethoxypyrimidin-2-yl)oxy]picolinate (Compound No. 337)

1.5 g (5 mmol) of 6-amino-3-[(4,6-dimethoxypyrimidin-2-yl)oxy]picolinic acid, 0.8 g (5 mmol) of carbonyldiimidazole and 0.25 g (3 mmol) of N-isopropylidenehydroxylamine were stirred and refluxed in dichloromethane for 4 hours. After completion of the reaction, the reaction mixture was poured into water, and the dichloromethane layer was separated, washed with water and dried. Then, the solvent was distilled off under reduced pressure. The residual oily product was purified by column chromatography to obtain the desired product as colorless transparent crystals.

Amount: 0.7 g (yield: 58.3%), melting point: 210°–214° C.

EXAMPLE 15

Preparation of S-ethyl 6-amino-3-[(4,6-dimethoxypyrimidin-2-yl)oxy]picolinthioate (Compound No. 344)

2.5 g (8.5 mmol) of 6-amino-3-[(4,6-dimethoxypyrimidin-2-yl)oxy]picolinic acid, 0.64 g (10.3 mmol) of ethylmercaptan, 2.8 g (17 mmol) of diethyl cyano phosphate and 1.73 g (17.1 mmol) of triethylamine were added to a THF solution, and the mixture was stirred at room temperature for 4 hours. After completion of the reaction, the reaction mixture was poured into water and extracted with ethyl acetate, followed by separation, washed with water and dried. Then, the solvent was distilled off, and the residual oily product was purified by column chromatography to obtain the desired product as colorless transparent crystals.

Amount: 1.0 g (yield: 34.7%), melting point: 115°–118° C.

EXAMPLE 16

Preparation of N'-methyl-N'-methoxy-3-[(4,6-dimethoxypyrimidin-2-yl)oxy]-6-(N,N-dimethylamino)picolinamide (Compound No. 349)

4.0 g (12 mmol) of 6-(N,N-dimethylamino)-3-[(4,6-dimethoxypyrimidin-2-yl)oxy]picolinic acid and 3.0 g (19 mmol) of carbonyl diimidazole were added to 30 ml of THF, and the mixture was stirred at room temperature for 4 hours. Then, the reaction mixture was poured into water and extracted with ethyl acetate. The extract was washed with water and dried. The solvent was distilled off, and the residual oily product was crystallized from diisopropyl ether to obtain 4.0 g (yield: 87%) of 6-(N,N-dimethylamino)-3-[(4,6-dimethoxypyrimidin-2-yl)oxy]picolinoylimidazole as a reaction intermediate. 1 g (2.7 mmol) of this intermediate, 0.3 g (3.7 mmol) of N-methoxy-N-methylamine hydrochloride and 0.8 g (7.5 mmol) of sodium carbonate were added to 50 ml of acetone, and the mixture was stirred at room temperature for 30 minutes. After completion of the reaction, the reaction mixture was poured into water and extracted with ethyl acetate. The extract was washed with water, dried and concentrated. Then, the residual oily product was crystallized from diisopropyl ether to obtain the desired product as colorless prism crystals.

Amount: 0.9 g (yield: 90%), melting point: 157°–161° C.

EXAMPLE 17

Peparation of methyl 1-methyl-6-(N,N-dimethylamino-(3-[(4,6-dimethoxypyrimidin-2-yl)oxy]picolinate iodide (Compound No. 369)

2.0 g (6.5 mmol) of methyl 3-[(4,6-dimethoxypyrimidin-2-yl)oxy]-6-(N,N-dimethylamino)picolinate was added to 100 ml of acetone, and 10 ml (160 mmol) of methyl iodide was added thereto. The mixture was refluxed under heating for 16 hours. The solvent was distilled off, and 300 ml of diethyl ether was added to the residue. Precipitated crystals were collected by filtration and washed with ethyl acetate to obtain the desired product.

Amount: 0.77 g (yield: 27%), melting point: 167°–169° C.

EXAMPLE 18

Preparation of methyl 6-(N-picolinoylamino)-3-[(4,6-dimethoxypyrimidin-2-yl)oxy]picolinate (Compound No. 277

2.0 g (6.5 mmol) of methyl 6-amino-3-[(4,6-dimethoxypyrimidin-2-yl)oxy]picolinate, 1.2 g (6.5 mmol) of picolinoyl chloride hydrochloride and 2.0 g (14.8 mmol) of potassium carbonate were added to 30 ml of MEK, and the mixture was refluxed for 6 hours under stirring. After completion of the reaction, the reaction mixture was poured into water and extracted with ethyl acetate. The extract was washed with water and dried. The solvent was distilled off to obtain crude crystals. The crude crystals were washed with diisopropyl ether-ethyl acetate to obtain the desired product as colorless needle-like crystals.

Amount: 1.1 g (yield: 40.7%), melting point: 146°–150° C.

EXAMPLE 19

Preparation of methyl 3-[(4,6-dimethoxypyrimidin-2-yl)oxy]-6-(isothiocyanato)picolinate (Compound No. 319

0.82 g (7.15 mmol) of thiophosgene was dropwise added at room temperature to a solution of 2 g (6.5 mmol) of methyl 6-amino-3-[(4,6-dimethoxypyrimidin-2-yl)oxy]picolinate in 70 ml of dichloromethane and 50 ml of water. The mixture was stirred at room temperature for two hours. After completion of the reaction, the dichloromethane layer was separated and washed with water. Then, the organic layer was dried and concentrated. The obtained residue was recrystallized from a mixture of dichloromethane and diisopropyl ether to obtain the desired product as slightly yellow transparent crystals.

Amount: 1.7 g (yield: 76.6%), melting point: 116°–117° C.

The starting material compounds for the compound of the present invention can be prepared in accordance with the following process P.

Process P

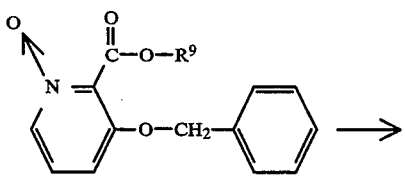

(XXXVII)

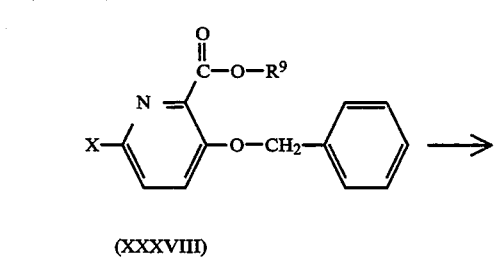

(XXXVIII)

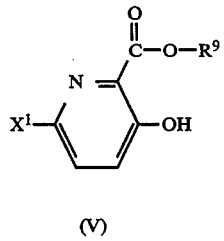

(V)

In the above formulas, $R^9$ and $X^1$ are as defined above.

Namely, the compound of the formula (XXXVII) is converted to the compound of the formula (XXXVIII) by an N,N-dialkylcarbamoyl chloride and a base, followed by catalytic hydrogenation with hydrogen to obtain the compound of the formula (V). The production of the compound of the formula (V) from the compound of the formula (XXXVII) can be conducted also by a method disclosed in Japanese Patent Application No. 302644/1991 by the present inventors. However, such a method as disclosed in this Japanese application is not necessarily a good method, since in addition to the material necessary for the present invention, a 6-cyano compound is produced in a large amount as a by-product by the use of trimethylsilylnitrile, and its separation and purification are cumbersome.

Now, the processes for producing the starting compounds and their intermediates will be described with reference to Reference Examples.

REFERENCE EXAMPLE 1

Preparation of methyl 3-benzyloxy-6-(N-N-dimethylamino)picolinate (Intermediate No. 1)

1.3 g (5 mmol) of methyl 3-benzyloxypicolinate N-oxide, 3.0 g (20 mmol) of sodium iodide, 0.65 g (5 mmol) of N,N-diisopropylethylamine and 0.7 g (6.5 mmol) of N,N-dimethylcarbamoyl chloride were added to 12.5 ml of acetonitrile, and the mixture was refluxed under heating for 30 minutes. After cooling, the reaction mixture was poured into water and extracted with ethyl acetate. The organic layer was washed with water, dried and concentrated. The residue thereby obtained was purified by silica gel column chromatography to obtain the desired product.

Amount: 0.85 g (yield: 57%), melting point: 71.5°–73° C.

REFERENCE EXAMPLE 2

Preparation of methyl 6-(N,N-dimethylamino)-3-hydroxypicolinate (Intermediate No. 2)

2.3 g (8 mmol) of methyl 3-benzyloxy-6-(N,N-dimethylamino)picolinate and 0.3 g of 10% palladium carbon were added to 100 ml of ethyl acetate, and the mixture was hydrogenated under atmospheric pressure. After completion of the reaction, the product was filtered and concentrated to obtain crystals.

Amount: 1.4 g (yield: 92%), melting point: 118.5°–120° C.

REFERENCE EXAMPLE 3

Preparation of 3-benzyloxy-6-(1-pyrrolidinyl)picolinic acid 6.48 g (25 mmol) of methyl 3-benzyloxypicolinate (N-oxide), 6.68 g (50 mmol) of 1-pyrrolidinylcarbonyl chloride, 6.46 g (50 mmol) of N,N-diisopropylethylamine and 7.49 g (50 mmol) of sodium iodide were refluxed under heating for two hours in 120 ml of acetonitrile. The solvent was distilled off, and water was added to the residue. The mixture was extracted with ethyl acetate, washed with a saturated sodium chloride aqueous solution and dried over anhydrous magnesium sulfate. The solvent was distilled off, and the obtained mixture was purified by silica gel column chromatography (ethyl acetate-n-hexane) to obtain the desired product.

Amount: 6.50 g (yield: 83%), melting point: 120°–121.5° C.

REFERENCE EXAMPLE 4

Preparation of methyl 3-hydroxy-6-(1-pyrrolidinyl)picolinate (Intermediate No. 11)

6.10 g (19.5 mmol) of methyl 3-benzyloxy-6-(1-pyrrolidinyl)picolinate was catalytically reduced in 50 ml of methanol and 100 ml of 1,2-dimethoxyethane in the presence of 1.5 g of 10% palladium carbon. The catalyst was filtered off, and the solvent was distilled off, and the residue was crystallized from diisopropyl ether-n-hexane to obtain the desired product.

Amount: 4.33 g (yield: 100%), melting point: 82.5°–84° C.

REFERENCE EXAMPLE 5

Preparation of methyl 6-azido-3-benzyloxypicolinate

To an acetonitrile (70 ml) solution of 10 g (38.57 mmol) of methyl 3-benzyloxypicolinate N-oxide in a 200 ml round bottomed flask, 8.9 g (7.7 mmol) of trimethylsilylazide and 4.1 g (38.57 mmol) of N,N-dimethylcarbamoyl chloride were added, and the mixture was refluxed for 12 hours. Then, 4.4 g (38.5 mmol) of trimethylsilylazide and 2.1 g (19.3 mmol) of N,N-dimethylcarbamoyl chloride were further added, and the mixture was refluxed for 12 hours. After cooling, the reaction mixture was gradually added to an ice-cooled saturated sodium hydrogen carbonate aqueous solution. Formed crystals were collected by filtration, washed with water, then dissolved in dichloromethane, dried and concentrated, and then recrystallized from ethanol to obtain 7.0 g (yield: 64%) of the desired product.

Colorless needle-like crystals, melting point: 88°–89° C.

REFERENCE EXAMPLE 6

Preparation of methyl 6-amino-3-hydroxypicolinate (Intermediate No. 3)

To a methanol (80 ml) suspension of 7 g (24.6 mmol) of methyl 6-azido-3-benzyloxypicolinate in a 200 ml round bottomed flask, 1 g of palladium carbon (10%) was added under a nitrogen gas stream, and 7.8 g (123 mmol) of ammonium formate was further added thereto. The mixture was stirred at room temperature for 12 hours. The catalyst was filtered off, and the filtrate was concentrated and dissolved in chloroform. The solvent was washed with water, dried and concentrated. Crystals thereby formed were collected by filtration and washed with diisopropyl ether to obtain 3.57 g (yield: 86.3%) of methyl 6-amino-3-hydroxypicolinate.

Yellow needle-like crystals, melting point: 170°–173° C.

Examples of such intermediates will be given in Table 6.

TABLE 6

$$X^1 \underset{\underset{OR^{18}}{}}{\overset{N}{\diagup}} COOCH_3$$

| Intermediate No. | $X^1$ | $R^{18}$ | m.p. (°C.) |
|---|---|---|---|
| 1 | $N(CH_3)_2$ | $CH_2$-phenyl | 71.5–73 |
| 2 | $N(CH_3)_2$ | H | 118.5–120 |
| 3 | $NH_2$ | H | 170–173 |
| 4 | $NH_2$ | $CH_2$-phenyl | |
| 5 | $CH_3NH$ | H | |
| 6 | $CH_3NH$ | $CH_2$-phenyl | |
| 7 | $CH_3C(O)N(CH_3)-$ | H | |
| 8 | $CH_3C(O)N(CH_3)-$ | $CH_2$-phenyl | |
| 9 | $N_3$ | H | |

TABLE 6-continued $$X^1 \diagup N \diagdown COOCH_3 \quad OR^{18}$$

| Intermediate No. | $X^1$ | $R^{18}$ | m.p. (°C.) |
|---|---|---|---|
| 10 | $N_3$ | $CH_2$—Ph | 88–89 |
| 11 | pyrrolidin-N— | H | 82.5–84 |
| 12 | pyrrolidin-N— | $CH_2$—Ph | 120–121.5 |

In the present invention, the starting materials of the formula (XII) and (XIV) can be prepared by the following methods. Herbicidal activities are observed also with the starting materials.

REFERENCE EXAMPLE 7

Preparation of methyl 6-amino-3-[(4,6-dimethoxypyrimidin-2-yl)oxy]picolinate 4.9 g (18 mmol) of 6-acetylamino-3-benzyloxypicoline aldehyde was added to 100 ml of acetone. 400 ml of an aqueous solution of 4.3 g (27 mmol) of potassium permanganate was added thereto, and the mixture was stirred at room temperature for one hour. Precipitated manganese dioxide was filtered off and washed with 100 ml of hot water. The filtrate was extracted with ethyl acetate, and the aqueous layer was neutralized with citric acid. Precipitated crystals were extracted with chloroform, washed with water, dried and concentrated. The crystals thereby obtained were washed with diisopropyl ether to obtain 6-acetylamino-3-benzyloxy picolinic acid.

Amount: 1.5 g (yield: 29%)

1.5 g (5.2 mmol) of the obtained 6-acetylamino-3-benzyloxypicolinic acid and 1.0 g (7 mmol) of methyl iodide were dissolved in 100 ml of DMF, and 20 ml of an aqueous solution of 0.53 g (6.3 mmol) of sodium hydrogen carbonate was added thereto. The mixture was reacted at 60° C. for 3 hours. The reaction solution was poured into water and extracted with ethyl acetate. The extract was washed with water, dried and concentrated. The crystals thereby obtained was washed with diisopropyl ether to obtain methyl 6-acetylamino-3-benzyloxypicolinate.

Amount: 1.57 g (yield: 90%)

1.57 g (4.7 mmol) of the obtained methyl 6-acetylamino-3-benzyloxypicolinate and 0.2 g of 10% palladium carbon were added to 100 ml of methanol, and the mixture was hydrogenated under atmospheric pressure. After completion of the reaction, the reaction mixture was filtered and concentrated to obtain crystals, which were washed with diisopropyl ether to obtain methyl 6-acetylamino-3-hydroxypicolinate.

Amount: 0.78 g (yield: 79%)

0.78 g (3.7 mmol) of the obtained methyl 6-acetylamino-3-hydroxypicolinate, 0.81 g (3.7 mmol) of 4,6-dimethoxy-2-methylsulfonylpyrimidine and 0.51 g (3.7 mmol) of potassium carbonate were added to 50 ml of DMF, and the mixture was reacted at 80° C. for two hours. After completion of the reaction, the reaction mixture was poured into water and extracted with diethyl ether. The extract was washed with water, dried and concentrated. The oily product thereby obtained was purified by column chromatography to obtain methyl 6-acetylamino-3-[(4,6-dimethoxypyrimidin-2-yl)oxy]picolinate.

Amount: 0.90 g (yield: 70%), melting point: 80°–85° C.

0.50 g (1.4 mmol) of the obtained methyl 6-acetylamino-3-[(4,6-dimethoxypyrimidin-2-yl)oxy]picolinate was added to 50 ml of boron trifluoride-methanol complex, and the mixture was refluxed under heating for 30 minutes. The solvent was distilled off, and the residue was poured into water, neutralized with sodium hydrogen carbonate and then extracted with chloroform. The extract was washed with water, dried and concentrated. The crystals thereby obtained, were washed with ethyl acetate:hexane=1:1 to obtain the desired product.

Amount: 0.36 g (yield: 82%), melting point: 67°–69° C.

REFERENCE EXAMPLE 8

Preparation of methyl 3-[(4,6-dimethoxypyrimdin-2-yl)oxy]-6-methylaminopicolinate Into a photoreaction flask having a capacity of 1 l, 20.0 g (60 mmol) of methyl 3-[(4,6-dimethoxypyrimidin-2-yl)oxy]-6-(N,N-dimethylamino)picolinate and 1,300 ml of chloroform were charged and irradiated by a 400 W high pressure mercury lamp for 24 hours. Chloroform was distilled off under reduced pressure, and the residue was purified by silica gel column chromatography (hexane-ethyl acetate=6:1 to 3:7) to obtain the desired product.

Amount: 2.10 g (yield: 10.7%)

REFERENCE EXAMPLE 9

Process for producing 3-[(4,6-dimethoxypyrimidin-2-yl)oxy]-6-methylaminopicolinic acid (First method).

Preparation of methyl 6-amino-3-[(4,6-dimethoxypyrimidin-2-yl)oxy]picolinate

A DMF suspension (50 ml) of 3.0 g (17.8 mmol) of methyl 6-amino-3-hydroxypicolinate, 3.9 g (17.8 mmol) of 2-methylsulfonyl-4,6-dimethoxypyrimidine and 1.23 g (8.9 mmol) of potassium carbonate in a 100 ml round bottomed flask, was stirred at 80° C. for 4 hours. The reaction mixture was poured into ice water and extracted with dichloromethane. The organic layer was washed with water, dried, concentrated and purified by silica gel chromatography (n-hexane/AcO-Et=1/1+0.1 MeOH) to obtain 4.43 g (yield: 81.3%) of the desired product.

Colorless prism crystals, melting point: 74°–75° C.

Preparation of methyl 6-(N-acetylamino)-3-[(4,6-dimethoxypyridin-2-yl)oxy]picolinate 318.9 g (1.04 mol) of methyl 6-amino-3-[(4,6-dimethoxypyrimidin-2-yl)oxy]picolinate and 157.6 g (1.14 mol) of potassium carbonate were dissolved in MEK, and 89.8 g (1.14 mol) of acetyl chloride was added thereto at room temperature. The mixture was refluxed under heating (75° C.) for two hours. MEK was concentrated to a half amount and then cooled. The reaction solution was poured into ice water and crystallized. Crystals thereby obtained was collected by filtration and washed with water. The crystals were dissolved in dichloromethane and subjected to liquid separation. The dichloromethane layer was dried over anhydrous magnesium sulfate and then concentrated. A small amount of diisopropyl ether were added thereto, and the mixture was cooled for crystallization. The crystals thereby obtained were recrystallized from 100 ml of ethanol. The crystals thereby obtained were washed with diisopropyl ether and then dried at 50° C. for 24 hours to obtain the desired product as a white powder.

Amount: 54.3 g, melting point: 128°–130.5° C., total amount 293.3 g (yield: 81%)

Preparation of methyl 6-(N-acetyl-N-methylamino)-3-[(4,6-dimethoxypyrimidin-2-yl)oxy]picolinate 30.4 g (0.76 mol) of sodium hydride was added to DMF, and 239 g (0.69 mol) of methyl 6-N-acetylamino-3-[(4,6-dimethoxypyrimidin-2-yl)oxy]picolinate was added thereto at a temperature of at most 10° C. The mixture was stirred at room temperature for 3 hours. After confirming completion of the generation of hydrogen, 146.9 g (1.04 mol) of methyl iodide was dropwise added thereto at a temperature of at most 10° C. The mixture was returned to room temperature and then stirred for one hour. The mixture was poured into ice water and subjected to crystallization, followed by filtration. The crystals were washed with water and dried to obtain 95.6 g (yield: 78%) of the desired product.

Colorless needle-like crystals, melting point: 119°–121° C.

Preparation of 3-[(4,6-dimethoxypyrimidin-2-yl)oxy]-6-methylaminopicolinic acid 195.6 g (0.54 mol) of methyl 6-(N-acetyl-N-methylamino)-3-[(4,6-dimethoxypyrimidin-2-yl)oxy]picolinate was dissolved in 1.5 l of methanol. The solution was added to 335 g of a 20% potassium hydroxide aqueous solution, and the mixture was stirred for one hour at 50° C. The reaction solution was concentrated, and 1 l of ice water was added thereto. The mixture was acidified (to about pH4) with an aqueous citric acid solution and left to cool. Precipitated crystals were collected by filtration and washed with cool water and diisopropyl ether. Then, the crystals were dissolved in 1 l of methanol, and 45.6 g (0.69 mol) of potassium hydroxide and 50 ml of water were added thereto. The mixture was stirred at room temperature for 28 hours. The reaction solution was concentrated, and ice water was added thereto. The mixture was acidified with an aqueous citric acid solution to obtain crude crystals. The crystals were washed with diisopropyl ether and then dried under reduced pressure at 90° C. for 24 hours to obtain 112 g (yield: 68%) of the desired product as a white powder.

Melting point: 172°–174° C.

Process for producing 3-[(4,6-dimethoxypyrimidin-2-yl)oxy]-6-methylaminopicolinic acid (Second method)

10.5 mg (0.0576 mmol) of methyl 6-methylamino-3-hydroxypicolinate, 11.6 mg (0.0532 mmol) of 2-methylsulfonyl-4,6-dimethoxypyrimidine, 8.8 mg (0.637 mmol) of potassium carbonate and 0.5 ml of dry dimethylsulfoxide were mixed. The mixture was stirred at room temperature for 5 hours, and then a 10% potassium hydroxide aqueous solution (corresponding to 90 mg, 0.160 mmol) was added thereto. The mixture was reacted at room temperature for one hour, and then 2.0 ml of water was added to the reaction mixture. Further, 1.0 ml of a 10% citric acid aqueous solution was added thereto, and the mixture was left to stand, whereby crystals precipitated. After being thoroughly precipitated, the crystals were filtered under suction and washed with water. The crystals were dried to obtain 3-[(4,6-dimethoxypyrimidin-2-yl)oxy]-6-methylaminopicolinic acid.

Colorless prism crystals, 13.7 mg (yield: 84.0%)

The herbicidal composition of the present invention comprises the picolinic acid derivative of the formula (I), (II), (III) and (IV) as an active ingredient.

The compound of the present invention may be used by itself as a herbicide. However, it may be used usually in the form of a formulation such as a dust, a wettable powder, an emulsifiable concentrate, a microgranule or a granule by blending it with a carrier which is commonly used for formulations, a surfactant, a dispersant or an adjuvant.

The carrier to be used for such formulations, may, for example, be a solid carrier such as Jeaklite, talc, bentonite, clay, kaolin, diatomaceous earth, fine silica, vermiculite, calcium carbonate, slaked lime, silica sand, ammonium sulfate or urea, or a liquid carrier such as isopropyl alcohol, xylene, cyclohexane or methylnaphthalene.

As the surfactant and dispersant, a metal salt of alkylbenzenesulfonic acid, a metal salt of dinaphthylmethane disulfonic acid, a salt of alcohol sulfuric acid ester, a salt of alkylaryl sulfonic acid, a salt of lignin sulfonic acid, a polyoxyethylene glycol ether, a polyoxyethylene alkylaryl ether or a polyoxyethylene sorbitol monoalkylate may, for example, be mentioned. The adjuvant may, for example, be carboxymethyl cellulose, polyethylene glycol or gum arabic.

In practical use, the herbicide may be diluted to a suitable concentration before application, or may be directly applied.

The herbicide of the present invention may be used for application to foliage, soil or water surface. The blending proportion of the active ingredient is suitably selected as the case requires. However, in a case of a dust or a granule, the proportion of the active ingredient is selected suitably within a range of from 0.01 to 10% by weight, preferably from 0.05 to 5% by weight. In a case of an emulsifiable concentrate or a wettable powder, the proportion is selected suitably within a range of from 1 to 50% by weight, preferably from 5 to 20% by weight.

The dose of the herbicide of the present invention varies depending upon the type of the compound, the weeds to be controlled, the germination tendency, the environmental conditions and the type of the formulation to be used. However, in the case of a dust or a granule which is used by itself, the dose of the active ingredient is selected suitably within a range of from 0.1 g to 5 kg, preferably from 1 g to 1 kg, per 10 ares. In a case of an emulsifiable concentrate or a wettable powder which is used in a liquid state, the dose of the active ingredient is selected suitably within a range of from 1 to 50,000 ppm, preferably from 10 to 10,000 ppm.

Further, the compound of the present invention may be used in combination with an insecticide, a fungicide, other herbicide, a plant growth controlling agent, a fertilizer or the like, as the case requires.

Now, the formulation method will be described with reference to typical Formulation Examples. The compounds, types of the additives and blending ratios are not limited to such specific Examples and may be changed within wide ranges. In the following description, "parts" means "parts by weight".

FORMULATION EXAMPLE 1 (Wettable powder)

To 10 parts by weight of Compound No. 14, 0.5 part of polyoxyethyleneoctylphenyl ether, 0.5 part of sodium β-naphthalene sulfonate-formalin condensate, 20 parts of diatomaceous earth and 69 parts of clay were mixed and pulverized to obtain a wettable powder.

FORMULATION EXAMPLE 2 (Wettable powder)

To 10 parts of Compound No. 83, 0.5 part of polyoxyethyleneoctylphenyl ether, 0.5 part of sodium β-naphthalene sulfonate-formalin condensate, 20 parts of diatomaceous earth, 5 parts of fine silica and 64 parts of clay were mixed and pulverized to obtain a wettable powder.

FORMULATION EXAMPLE 3 (Wettable powder formulated with calcium carbonate)

To 10 parts of Compound No. 277, 0.5 part of polyoxyethyleneoctylphenyl ether, 0.5 part of sodium α-naphthalene sulfonate-formalin condensate, 20 parts of diatomaceous earth, 5 parts of fine silica and 64 parts of calcium carbonate, were mixed and pulverized to obtain a wettable powder.

FORMULATION EXAMPLE 4 (Emulsifiable concentrate)

To 30 parts of Compound No. 346, 60 parts of a mixture comprising equal amounts of xylene and isophorone and 10 parts of a mixture comprising a polyoxyethylene sorbitol alkylate surfactant, a polyoxyethylenealkylaryl polymer and an alkylaryl sulfonate, were added, and the mixture was thoroughly stirred to obtain an emulsifiable concentrate.

FORMULATION EXAMPLE 5 (Granule)

10 parts of Compound No. 337, 80 parts of a bulking agent comprising a 1:3 mixture of talc and bentonite, 5 parts of fine silica, 5 parts of a mixture comprising a polyoxyethylene sorbitol alkylate surfactant, a polyoxyethylenealkylaryl polymer and an alkylaryl sulfonate and 10 parts of water were mixed and thoroughly kneaded to obtain a paste, which was extruded from sieve apertures with a diameter of 0.7 mm. The extruded product was dried and then cut into a length of from 0.5 to 1 mm to obtain granules.

Now, the herbicidal effects of the compounds of the present invention will be described with reference to Test Examples.

TEST EXAMPLE 1 (Test on herbicidal effects by paddy field soil treatment)

In a plastic pot (surface area: 100 cm$^2$) filled with paddy field soil, barnyardgrass (Eo), monochoria (Mo) and bulrush (Sc) were sown after puddling and leveling, and flooded to a water depth of 3 cm. Next day, a wettable powder prepared in accordance with Formulation Example 1 was diluted with water and applied dropwise to the water surface. The dose was 100 g of the active ingredient per 10 ares. The plants were then cultured in a green house, and the evaluation of the herbicidal effects was conducted on the 21st day after the application in accordance with the standards as identified in Table 7. The results are shown in the following Table 8.

TABLE 7

| Index No. | Herbicidal effects (growth-controlling degree) or phytotoxicity |
|---|---|
| 5 | Herbicidal effect or phytotoxicity: at least 90% |
| 4 | Herbicidal effect or phytotoxicity: at least 70% and less than 90% |
| 3 | Herbicidal effect or phytotoxicity: at least 50% and less than 70% |
| 2 | Herbicidal effect or phytotoxicity: at least 30% and less than 50% |
| 1 | Herbicidal effect or phytotoxicity: at least 10 and less than 30% |
| 0 | Herbicidal effect or phytotoxicity: 0 to less than 10% |

TABLE 8

| | Herbicidal effect | | |
|---|---|---|---|
| Comp. No. | Eo | Mo | Sc |
| 13 | 5 | 5 | 5 |
| 14 | 5 | 5 | 5 |
| 15 | 5 | 5 | 3 |
| 16 | 5 | 5 | 3 |
| 20 | 5 | 5 | 5 |
| 21 | 5 | 5 | 5 |
| 24 | 5 | 5 | 5 |
| 25 | 5 | 5 | 5 |
| 26 | 5 | 5 | 5 |
| 39 | 5 | 5 | 5 |
| 40 | 5 | 5 | 5 |
| 41 | 5 | 5 | 5 |
| 42 | 5 | 5 | 5 |
| 43 | 5 | 5 | 5 |
| 44 | 5 | 5 | 5 |
| 49 | 5 | 5 | 5 |
| 50 | 5 | 5 | 5 |
| 51 | 5 | 5 | 5 |
| 52 | 5 | 5 | 5 |
| 53 | 5 | 5 | 5 |
| 54 | 5 | 5 | 5 |
| 55 | 5 | 5 | 5 |
| 56 | 5 | 5 | 5 |
| 57 | 5 | 5 | 5 |
| 58 | 5 | 5 | 5 |
| 62 | 5 | 5 | 3 |
| 63 | 5 | 5 | 3 |
| 64 | 5 | 5 | 3 |
| 65 | 5 | 5 | 5 |
| 68 | 5 | 5 | 5 |
| 69 | 5 | 5 | 5 |
| 73 | 5 | 5 | 5 |
| 76 | 5 | 5 | 5 |
| 77 | 5 | 5 | 5 |
| 78 | 5 | 5 | 5 |
| 80 | 5 | 5 | 3 |
| 81 | 5 | 5 | 5 |
| 84 | 5 | 5 | 3 |
| 86 | 5 | 5 | 5 |
| 87 | 5 | 5 | 5 |
| 88 | 5 | 5 | 5 |

TABLE 8-continued

| Comp. No. | Herbicidal effect | | |
|---|---|---|---|
| | Eo | Mo | Sc |
| 89 | 5 | 5 | 5 |
| 91 | 5 | 5 | 5 |
| 92 | 5 | 5 | 5 |
| 93 | 5 | 5 | 5 |
| 102 | 5 | 5 | 5 |
| 104 | 5 | 5 | 5 |
| 105 | 5 | 5 | 5 |
| 108 | 5 | 5 | 5 |
| 109 | 5 | 5 | 5 |
| 130 | 5 | 5 | 5 |
| 134 | 5 | 5 | 5 |
| 136 | 5 | 5 | 5 |
| 137 | 5 | 5 | 5 |
| 138 | 5 | 5 | 5 |
| 139 | 5 | 5 | 5 |
| 141 | 5 | 5 | 5 |
| 143 | 5 | 5 | 5 |
| 144 | 5 | 5 | 5 |
| 145 | 5 | 5 | 5 |
| 146 | 5 | 5 | 5 |
| 147 | 5 | 5 | 5 |
| 148 | 5 | 5 | 5 |
| 150 | 5 | 5 | 5 |
| 151 | 5 | 5 | 5 |
| 152 | 5 | 5 | 5 |
| 158 | 5 | 5 | 5 |
| 160 | 5 | 5 | 5 |
| 164 | 5 | 5 | 5 |
| 172 | 5 | 5 | 5 |
| 173 | 5 | 5 | 5 |
| 174 | 5 | 5 | 5 |
| 175 | 5 | 5 | 5 |
| 176 | 5 | 5 | 5 |
| 201 | 5 | 5 | 5 |
| 204 | 5 | 5 | 5 |
| 205 | 5 | 5 | 5 |
| 206 | 5 | 5 | 5 |
| 207 | 5 | 5 | 5 |
| 208 | 5 | 5 | 5 |
| 213 | 5 | 5 | 5 |
| 214 | 5 | 5 | 5 |
| 215 | 5 | 5 | 5 |
| 216 | 5 | 5 | 5 |
| 218 | 5 | 5 | 5 |
| 225 | 5 | 5 | 5 |
| 226 | 5 | 5 | 5 |
| 229 | 5 | 5 | 5 |
| 230 | 5 | 5 | 5 |
| 257 | 5 | 5 | 5 |
| 276 | 5 | 5 | 5 |
| 277 | 5 | 5 | 5 |
| 278 | 5 | 5 | 5 |
| 280 | 5 | 5 | 5 |
| 282 | 5 | 5 | 5 |
| 304 | 5 | 5 | 5 |
| 312 | 5 | 5 | 5 |
| 313 | 5 | 5 | 5 |
| 316 | 5 | 5 | 5 |
| 317 | 5 | 5 | 5 |
| 319 | 5 | 5 | 5 |
| 321 | 5 | 5 | 5 |
| 336 | 5 | 5 | 5 |
| 337 | 5 | 5 | 5 |
| 338 | 5 | 5 | 5 |
| 339 | 5 | 5 | 5 |
| 340 | 5 | 5 | 5 |
| 341 | 5 | 5 | 5 |
| 342 | 5 | 5 | 5 |
| 343 | 5 | 5 | 5 |
| 344 | 5 | 5 | 5 |
| 346 | 5 | 5 | 5 |
| 347 | 5 | 5 | 5 |
| 348 | 5 | 5 | 5 |
| 351 | 5 | 5 | 5 |
| 352 | 5 | 5 | 5 |
| 353 | 5 | 5 | 5 |
| 354 | 5 | 5 | 5 |
| 355 | 5 | 5 | 3 |
| 356 | 5 | 5 | 5 |

TEST EXAMPLE 2 (Test on herbicidal effects by upland field soil treatment)

In a plastic pot (surface area: 120 cm$^2$) filled with upland field soil, barnyardgrass (Ec), pale smartweed (Po), slender amaranth (Am), common lambsquarters (Ch) and rice flatsedge (Ci) were sown and covered with soil. A wettable powder prepared in accordance with Formulation Example 1 was diluted with water and applied uniformly to the soil surface by a small-sized sprayer in an amount of 100 l/10 ares so as to apply 100 g of the active ingredient per 10 ares. The plants were then cultured in a green house, and the evaluation of the herbicidal effects was conducted on the 21st day after the application in accordance with the standards as identified in the above Table 5. The results are shown in the following Table 9.

TABLE 9

| Comp. No. | Herbicidal effect | | | | |
|---|---|---|---|---|---|
| | Ec | Po | Am | Ch | Ci |
| 13 | 5 | 5 | 5 | 5 | 5 |
| 14 | 5 | 5 | 5 | 5 | 5 |
| 16 | 5 | 5 | 5 | 5 | 5 |
| 19 | 5 | 5 | 5 | 5 | 5 |
| 20 | 5 | 5 | 5 | 5 | 5 |
| 21 | 5 | 5 | 5 | 5 | 5 |
| 24 | 5 | 5 | 5 | 5 | 5 |
| 25 | 5 | 5 | 5 | 5 | 5 |
| 26 | 5 | 5 | 5 | 5 | 5 |
| 39 | 5 | 5 | 5 | 5 | 5 |
| 40 | 5 | 5 | 5 | 5 | 5 |
| 41 | 5 | 5 | 5 | 5 | 5 |
| 42 | 5 | 5 | 5 | 5 | 5 |
| 43 | 5 | 5 | 5 | 5 | 5 |
| 44 | 5 | 5 | 5 | 5 | 5 |
| 49 | 5 | 5 | 5 | 5 | 5 |
| 50 | 5 | 5 | 5 | 5 | 5 |
| 51 | 5 | 5 | 5 | 5 | 5 |
| 52 | 5 | 5 | 5 | 5 | 5 |
| 53 | 5 | 5 | 5 | 5 | 5 |
| 54 | 5 | 5 | 5 | 5 | 5 |
| 55 | 5 | 5 | 5 | 5 | 5 |
| 56 | 5 | 5 | 5 | 5 | 5 |
| 57 | 5 | 5 | 5 | 5 | 5 |
| 65 | 5 | 5 | 5 | 5 | 5 |
| 68 | 5 | 5 | 5 | 5 | 5 |
| 69 | 5 | 5 | 5 | 5 | 5 |
| 72 | 5 | 5 | 5 | 5 | 5 |
| 75 | 5 | 5 | 5 | 5 | 5 |
| 77 | 5 | 5 | 5 | 5 | 5 |
| 83 | 5 | 5 | 5 | 5 | 5 |
| 86 | 5 | 5 | 5 | 5 | 5 |
| 87 | 5 | 5 | 5 | 5 | 5 |
| 88 | 5 | 5 | 5 | 5 | 5 |
| 89 | 5 | 4 | 5 | 5 | 5 |
| 92 | 5 | 5 | 5 | 5 | 5 |
| 93 | 5 | 5 | 5 | 5 | 5 |
| 107 | 5 | 5 | 5 | 5 | 5 |
| 134 | 5 | 5 | 5 | 5 | 5 |
| 137 | 5 | 5 | 5 | 5 | 5 |
| 138 | 5 | 5 | 5 | 5 | 5 |
| 143 | 5 | 5 | 5 | 5 | 5 |
| 144 | 5 | 5 | 5 | 5 | 5 |
| 145 | 5 | 5 | 5 | 5 | 5 |
| 146 | 5 | 5 | 5 | 5 | 5 |
| 147 | 5 | 5 | 5 | 5 | 5 |
| 148 | 5 | 5 | 5 | 5 | 5 |
| 152 | 5 | 5 | 5 | 5 | 5 |
| 159 | 4 | 4 | 5 | 5 | 5 |
| 160 | 5 | 5 | 5 | 5 | 5 |

TABLE 9-continued

| Comp. No. | Herbicidal effect | | | | |
|---|---|---|---|---|---|
| | Ec | Po | Am | Ch | Ci |
| 173 | 5 | 5 | 5 | 5 | 5 |
| 174 | 5 | 5 | 5 | 5 | 5 |
| 175 | 5 | 5 | 5 | 5 | 5 |
| 176 | 5 | 5 | 5 | 5 | 5 |
| 204 | 5 | 5 | 5 | 5 | 5 |
| 207 | 5 | 5 | 5 | 5 | 5 |
| 208 | 5 | 5 | 5 | 5 | 5 |
| 213 | 5 | 5 | 5 | 5 | 5 |
| 214 | 5 | 5 | 5 | 5 | 5 |
| 215 | 4 | 5 | 5 | 5 | 5 |
| 217 | 5 | 5 | 5 | 5 | 5 |
| 218 | 4 | 5 | 5 | 5 | 5 |
| 221 | 5 | 5 | 5 | 5 | 5 |
| 222 | 5 | 5 | 5 | 5 | 5 |
| 223 | 5 | 5 | 5 | 5 | 5 |
| 224 | 4 | 5 | 5 | 5 | 5 |
| 225 | 5 | 5 | 5 | 5 | 5 |
| 226 | 5 | 5 | 5 | 5 | 5 |
| 227 | 5 | 4 | 5 | 5 | 5 |
| 229 | 5 | 5 | 5 | 5 | 5 |
| 230 | 5 | 5 | 5 | 5 | 5 |
| 258 | 5 | 5 | 5 | 5 | 5 |
| 262 | 4 | 5 | 5 | 5 | 5 |
| 266 | 5 | 5 | 5 | 5 | 5 |
| 276 | 5 | 5 | 5 | 5 | 5 |
| 277 | 5 | 5 | 5 | 5 | 5 |
| 278 | 5 | 5 | 5 | 5 | 5 |
| 313 | 5 | 5 | 5 | 5 | 5 |
| 316 | 5 | 5 | 5 | 5 | 5 |
| 317 | 5 | 5 | 5 | 5 | 5 |
| 318 | 5 | 5 | 5 | 5 | 5 |
| 319 | 4 | 5 | 5 | 5 | 5 |
| 334 | 5 | 5 | 5 | 5 | 5 |
| 336 | 5 | 5 | 5 | 5 | 5 |
| 337 | 5 | 5 | 5 | 5 | 5 |
| 338 | 5 | 5 | 5 | 5 | 5 |
| 339 | 5 | 5 | 5 | 5 | 5 |
| 340 | 5 | 5 | 5 | 5 | 5 |
| 341 | 5 | 5 | 5 | 5 | 5 |
| 342 | 5 | 5 | 5 | 5 | 5 |
| 343 | 5 | 5 | 5 | 5 | 5 |
| 344 | 5 | 5 | 5 | 5 | 5 |
| 346 | 5 | 5 | 5 | 5 | 5 |
| 348 | 5 | 5 | 5 | 5 | 5 |
| 352 | 5 | 5 | 5 | 5 | 5 |
| 353 | 5 | 5 | 5 | 5 | 5 |
| 354 | 5 | 5 | 5 | 5 | 5 |
| 355 | 5 | 4 | 4 | 5 | 5 |
| 356 | 5 | 4 | 4 | 5 | 5 |

EXAMPLE 3 (Test on herbicidal effects by upland field foliage treatment)

In a plastic pot (surface area: 120 cm$^2$) filled with upland field soil, barnyardgrass (Ec), pale smartweed (Po), slender amaranth (Am), common lambsquarters (Ch) and rice flatsedge (Ci) were sown and covered with soil and were cultured in a green house for 2 weeks. A wettable powder prepared in accordance with Formulation Example 1 was diluted with water and applied onto the entire foliages of the plants from above by a small-sized sprayer in an amount of 100 l/10 ares so as to apply 100 g of the active ingredient per 10 ares. The plants were then cultured in the green house, and the evaluation of the herbicidal effects was conducted on the 14th day after the treatment in accordance with the standards as identified in the above Table 5. The results are shown in the following Table 10.

TABLE 10

| Comp. No. | Herbicidal effect | | | | |
|---|---|---|---|---|---|
| | Ec | Po | Am | Ch | Ci |
| 13 | 5 | 5 | 5 | 5 | 5 |
| 14 | 5 | 5 | 5 | 5 | 5 |
| 16 | 5 | 5 | 5 | 5 | 5 |
| 18 | 5 | 5 | 5 | 5 | 5 |
| 19 | 5 | 5 | 5 | 5 | 5 |
| 20 | 5 | 5 | 5 | 5 | 5 |
| 21 | 5 | 5 | 5 | 5 | 5 |
| 24 | 5 | 5 | 5 | 5 | 5 |
| 25 | 5 | 5 | 5 | 5 | 5 |
| 26 | 5 | 5 | 5 | 5 | 5 |
| 39 | 5 | 5 | 5 | 5 | 5 |
| 40 | 5 | 5 | 5 | 5 | 5 |
| 41 | 5 | 5 | 5 | 5 | 5 |
| 42 | 5 | 5 | 5 | 5 | 5 |
| 43 | 5 | 5 | 5 | 5 | 5 |
| 44 | 5 | 5 | 5 | 5 | 5 |
| 49 | 5 | 5 | 5 | 5 | 5 |
| 50 | 5 | 5 | 5 | 5 | 5 |
| 51 | 5 | 5 | 5 | 5 | 5 |
| 52 | 5 | 5 | 5 | 5 | 5 |
| 53 | 5 | 5 | 5 | 5 | 5 |
| 54 | 5 | 5 | 5 | 5 | 5 |
| 55 | 5 | 5 | 5 | 5 | 5 |
| 56 | 5 | 5 | 5 | 5 | 5 |
| 57 | 5 | 5 | 5 | 5 | 5 |
| 62 | 5 | 5 | 5 | 5 | 5 |
| 63 | 5 | 5 | 5 | 5 | 5 |
| 64 | 5 | 5 | 5 | 5 | 5 |
| 65 | 5 | 5 | 5 | 5 | 5 |
| 68 | 5 | 5 | 5 | 5 | 5 |
| 69 | 5 | 5 | 5 | 5 | 5 |
| 72 | 5 | 5 | 5 | 5 | 5 |
| 73 | 5 | 5 | 5 | 5 | 5 |
| 74 | 5 | 5 | 5 | 5 | 5 |
| 75 | 5 | 5 | 5 | 5 | 5 |
| 76 | 5 | 5 | 5 | 5 | 5 |
| 77 | 5 | 5 | 5 | 5 | 5 |
| 79 | 5 | 5 | 5 | 5 | 5 |
| 80 | 5 | 5 | 5 | 5 | 5 |
| 83 | 5 | 5 | 5 | 5 | 5 |
| 84 | 5 | 5 | 5 | 4 | 4 |
| 85 | 5 | 5 | 5 | 4 | 5 |
| 86 | 5 | 5 | 5 | 5 | 5 |
| 87 | 5 | 5 | 5 | 5 | 5 |
| 88 | 5 | 5 | 5 | 5 | 5 |
| 89 | 5 | 5 | 5 | 5 | 5 |
| 90 | 5 | 5 | 5 | 5 | 5 |
| 91 | 5 | 5 | 5 | 5 | 5 |
| 92 | 5 | 5 | 5 | 5 | 5 |
| 93 | 5 | 5 | 5 | 5 | 5 |
| 96 | 5 | 5 | 4 | 4 | 4 |
| 97 | 5 | 5 | 5 | 4 | 4 |
| 100 | 5 | 5 | 5 | 5 | 3 |
| 102 | 5 | 5 | 5 | 5 | 5 |
| 103 | 5 | 5 | 5 | 5 | 5 |
| 104 | 5 | 5 | 5 | 5 | 5 |
| 105 | 5 | 5 | 5 | 5 | 5 |
| 106 | 5 | 5 | 5 | 5 | 5 |
| 107 | 5 | 5 | 5 | 5 | 5 |
| 108 | 5 | 5 | 5 | 5 | 5 |
| 109 | 5 | 5 | 5 | 5 | 5 |
| 113 | 5 | 5 | 5 | 5 | 4 |
| 114 | 5 | 5 | 5 | 5 | 4 |
| 115 | 5 | 5 | 5 | 5 | 4 |
| 118 | 5 | 5 | 5 | 5 | 5 |
| 119 | 5 | 5 | 5 | 5 | 5 |
| 120 | 5 | 5 | 5 | 5 | 5 |
| 122 | 5 | 5 | 5 | 5 | 5 |
| 126 | 5 | 5 | 5 | 4 | 5 |
| 129 | 5 | 5 | 5 | 5 | 5 |
| 133 | 5 | 5 | 5 | 5 | 5 |
| 134 | 5 | 5 | 5 | 5 | 5 |
| 135 | 5 | 5 | 5 | 5 | 5 |
| 136 | 5 | 5 | 5 | 5 | 5 |
| 137 | 5 | 5 | 5 | 5 | 5 |
| 138 | 5 | 5 | 5 | 5 | 5 |
| 139 | 5 | 5 | 5 | 5 | 5 |
| 140 | 5 | 5 | 5 | 5 | 5 |
| 141 | 5 | 5 | 5 | 4 | 5 |
| 143 | 5 | 5 | 5 | 5 | 5 |

TABLE 10-continued

| Comp. No. | Ec | Po | Am | Ch | Ci |
|---|---|---|---|---|---|
| 144 | 5 | 5 | 5 | 5 | 5 |
| 145 | 5 | 5 | 5 | 5 | 5 |
| 146 | 5 | 5 | 5 | 5 | 5 |
| 147 | 5 | 5 | 5 | 5 | 5 |
| 148 | 5 | 5 | 5 | 5 | 5 |
| 151 | 5 | 5 | 5 | 5 | 5 |
| 152 | 5 | 5 | 5 | 5 | 5 |
| 153 | 5 | 5 | 5 | 5 | 5 |
| 154 | 5 | 5 | 5 | 5 | 5 |
| 155 | 5 | 5 | 5 | 5 | 5 |
| 156 | 5 | 5 | 5 | 5 | 5 |
| 158 | 5 | 5 | 5 | 5 | 5 |
| 159 | 5 | 5 | 5 | 5 | 5 |
| 160 | 5 | 5 | 5 | 5 | 5 |
| 163 | 5 | 5 | 5 | 5 | 5 |
| 164 | 5 | 5 | 5 | 5 | 5 |
| 172 | 5 | 5 | 5 | 5 | 5 |
| 173 | 5 | 5 | 5 | 5 | 5 |
| 174 | 5 | 5 | 5 | 5 | 5 |
| 175 | 5 | 5 | 5 | 5 | 5 |
| 176 | 5 | 5 | 5 | 5 | 5 |
| 193 | 5 | 5 | 5 | 5 | 5 |
| 201 | 5 | 5 | 5 | 5 | 5 |
| 204 | 5 | 5 | 5 | 5 | 5 |
| 205 | 5 | 5 | 5 | 5 | 5 |
| 206 | 5 | 5 | 5 | 5 | 5 |
| 207 | 5 | 5 | 5 | 5 | 5 |
| 208 | 5 | 5 | 5 | 5 | 5 |
| 213 | 5 | 5 | 5 | 5 | 5 |
| 214 | 5 | 5 | 5 | 5 | 5 |
| 215 | 5 | 5 | 5 | 5 | 5 |
| 216 | 5 | 5 | 5 | 5 | 5 |
| 217 | 5 | 5 | 5 | 5 | 5 |
| 218 | 5 | 5 | 5 | 5 | 5 |
| 219 | 5 | 5 | 5 | 5 | 5 |
| 220 | 5 | 5 | 5 | 5 | 5 |
| 221 | 5 | 5 | 5 | 5 | 5 |
| 222 | 5 | 5 | 5 | 5 | 5 |
| 223 | 5 | 5 | 5 | 5 | 5 |
| 225 | 5 | 5 | 5 | 5 | 5 |
| 226 | 5 | 5 | 5 | 5 | 5 |
| 227 | 5 | 5 | 5 | 5 | 5 |
| 228 | 5 | 5 | 5 | 5 | 5 |
| 229 | 5 | 5 | 5 | 5 | 5 |
| 230 | 5 | 5 | 5 | 5 | 5 |
| 255 | 5 | 5 | 5 | 5 | 5 |
| 256 | 5 | 5 | 5 | 5 | 5 |
| 257 | 5 | 5 | 5 | 5 | 5 |
| 258 | 5 | 5 | 5 | 5 | 5 |
| 259 | 5 | 5 | 5 | 5 | 5 |
| 260 | 5 | 5 | 5 | 5 | 5 |
| 261 | 5 | 5 | 5 | 5 | 5 |
| 262 | 5 | 5 | 5 | 5 | 4 |
| 263 | 5 | 5 | 5 | 5 | 4 |
| 264 | 5 | 5 | 5 | 5 | 3 |
| 265 | 5 | 5 | 5 | 5 | 3 |
| 266 | 5 | 5 | 5 | 5 | 5 |
| 276 | 5 | 5 | 5 | 5 | 5 |
| 277 | 5 | 5 | 5 | 5 | 5 |
| 278 | 5 | 5 | 5 | 5 | 5 |
| 279 | 5 | 5 | 5 | 5 | 5 |
| 280 | 5 | 5 | 5 | 5 | 5 |
| 281 | 5 | 5 | 5 | 5 | 5 |
| 282 | 5 | 5 | 5 | 5 | 5 |
| 290 | 5 | 5 | 5 | 5 | 4 |
| 300 | 4 | 4 | 5 | 5 | 4 |
| 301 | 5 | 5 | 5 | 5 | 4 |
| 304 | 5 | 5 | 5 | 5 | 5 |
| 310 | 5 | 5 | 5 | 5 | 5 |
| 311 | 5 | 5 | 5 | 5 | 5 |
| 312 | 5 | 5 | 5 | 5 | 5 |
| 313 | 5 | 5 | 5 | 5 | 5 |
| 316 | 5 | 5 | 5 | 5 | 5 |
| 317 | 5 | 5 | 5 | 5 | 5 |
| 318 | 5 | 5 | 5 | 5 | 5 |
| 319 | 5 | 5 | 5 | 5 | 5 |
| 320 | 5 | 5 | 5 | 5 | 5 |
| 321 | 5 | 5 | 5 | 5 | 5 |
| 334 | 5 | 5 | 5 | 5 | 5 |
| 335 | 5 | 5 | 5 | 5 | 5 |
| 336 | 5 | 5 | 5 | 5 | 5 |
| 337 | 5 | 5 | 5 | 5 | 5 |
| 338 | 5 | 5 | 5 | 5 | 5 |
| 339 | 5 | 5 | 5 | 5 | 5 |
| 340 | 5 | 5 | 5 | 5 | 5 |
| 342 | 5 | 5 | 5 | 5 | 5 |
| 343 | 5 | 5 | 5 | 5 | 5 |
| 344 | 5 | 5 | 5 | 5 | 5 |
| 346 | 5 | 5 | 5 | 5 | 5 |
| 347 | 5 | 5 | 5 | 5 | 5 |
| 348 | 5 | 5 | 5 | 5 | 5 |
| 349 | 5 | 5 | 5 | 5 | 5 |
| 350 | 5 | 5 | 5 | 5 | 5 |
| 351 | 5 | 5 | 5 | 5 | 5 |
| 352 | 5 | 5 | 5 | 5 | 5 |
| 353 | 5 | 5 | 5 | 5 | 5 |
| 354 | 5 | 5 | 5 | 5 | 5 |
| 355 | 5 | 5 | 5 | 5 | 5 |
| 356 | 5 | 5 | 5 | 5 | 5 |
| 369 | 5 | 4 | 5 | 4 | 4 |

TEST EXAMPLE 4 (Test on herbicidal effects by upland field foliage treatment at a low dose)

In a plastic pot (surface area: 600 cm$^2$) filled with upland field soil, barnyardgrass (Ec), johnsongrass (So), pale smartweed (Po), slender amaranth (Am) and common lambsquarters (Ch) were sown and cultured in a green house for 2 weeks. A predetermined amount of a wettable powder prepared in accordance with Formulation Example 1 was diluted with water and applied onto the entire foliages of the plants from above by a small-sized sprayer in an amount of 100 l/10 ares. The plants were then cultured in the green house, and the evaluation of the herbicidal effects was conducted on the 14th day after the application in accordance with the standards as identified in the above Table 5. As comparative herbicides, compounds identified below were used. The results are shown in the following Table 11.

Comparative herbicide A (Compound disclosed in PCT Patent Publication WO-9207846-A1) (Compound No. 38):

Isopropyl 3-[(4,6-dimethoxypyrimidin-2-yl)oxy]-6-(N,N-dimethylamino)picolinate

Comparative herbicide B (Compound disclosed in PCT Patent Application WO-9207846-A1) (Compound No. 63):

Methyl 3-[(4,6-dimethoxypyrimidin-2-yl)oxy]-6-amino-picolinate

TABLE 11

| Comp. No. | Dose of active ingredient ($g^{ai}$/10a) | Herbicidal effect | | | | |
|---|---|---|---|---|---|---|
| | | Ec | So | Po | Am | Ch |
| Comparative Comp. A | 6.3 | 5 | 5 | 5 | 5 | 5 |
| | 1.6 | 2 | 3 | 3 | 3 | 3 |
| | 0.4 | 0 | 0 | 0 | 2 | 3 |
| Comparative Comp. B | 6.3 | 5 | 5 | 5 | 5 | 5 |
| | 1.6 | 4 | 4 | 4 | 5 | 4 |
| | 0.4 | 2 | 3 | 3 | 3 | 2 |
| 14 | 0.4 | 5 | 5 | 5 | 5 | 5 |
| 24 | 0.4 | 5 | 5 | 5 | 5 | 5 |
| 25 | 0.4 | 5 | 5 | 5 | 5 | 5 |
| 26 | 0.4 | 5 | 5 | 5 | 5 | 5 |
| 39 | 0.4 | 5 | 3 | 5 | 5 | 3 |
| 40 | 0.4 | 5 | 5 | 3 | 3 | 3 |
| 44 | 0.4 | 5 | 5 | 5 | 5 | 5 |
| 51 | 0.4 | 5 | 5 | 5 | 5 | 3 |

TABLE 11-continued

| Comp. No. | Dose of active ingredient ($g^{ai}$/10a) | Ec | So | Po | Am | Ch |
|---|---|---|---|---|---|---|
| 52 | 0.4 | 5 | 5 | 5 | 5 | 5 |
| 53 | 0.4 | 5 | 5 | 5 | 5 | 5 |
| 55 | 0.4 | 5 | 5 | 5 | 5 | 5 |
| 72 | 0.4 | 3 | 5 | 3 | 5 | 5 |
| 77 | 0.4 | 5 | 5 | 4 | 3 | 4 |
| 83 | 0.4 | 5 | 5 | 5 | 5 | 5 |
| 93 | 0.4 | 3 | 5 | 5 | 5 | 3 |
| 207 | 0.4 | 4 | 4 | 5 | 5 | 5 |
| 208 | 0.4 | 3 | 5 | 5 | 5 | 4 |
| 226 | 0.4 | 4 | 5 | 5 | 4 | 3 |
| 276 | 0.4 | 5 | 5 | 5 | 5 | 5 |
| 277 | 0.4 | 5 | 5 | 5 | 5 | 4 |
| 278 | 0.4 | 5 | 5 | 5 | 5 | 5 |
| 336 | 0.4 | 5 | 5 | 5 | 5 | 3 |
| 337 | 0.4 | 5 | 5 | 5 | 5 | 5 |
| 339 | 0.4 | 5 | 5 | 5 | 5 | 3 |
| 340 | 0.4 | 5 | 5 | 5 | 5 | 5 |
| 341 | 0.4 | 5 | 5 | 5 | 5 | 3 |
| 342 | 0.4 | 5 | 5 | 5 | 5 | 5 |
| 343 | 0.4 | 5 | 5 | 5 | 5 | 4 |
| 344 | 0.4 | 5 | 5 | 5 | 5 | 4 |
| 346 | 0.4 | 5 | 5 | 3 | 5 | 5 |
| 352 | 0.4 | 5 | 5 | 5 | 5 | 5 |
| 353 | 0.4 | 5 | 5 | 5 | 5 | 5 |

The compound of the formula (I) of the present invention has excellent herbicidal effects over a wide range of from the pre-emergence to the growing stage against various troublesome weeds grown in upland field including broadleaf weeds such as pale smartweed (polygonumlapathifolium), slender amaranth (*Amaranthus viridis*), common lambsquarters (Chenopodiumalbum), chickweed (*Stellaria media*), velveltleaf (*Abutilon theophrasti*), prickly sida (Sida spinosa), America tsunokusamune (Sesbania exaltata Cory), morningglory (Pomoea sp.) and common cocklebur (Xanthumstrumarium), perennial and annual cyperaceous weeds such as purple nutsedge (*Cyperus rotundus*), yellow nutsedge, Kyllingabrevifolia, umbrella plant (Cyperusmicroiria) and rice flatsedge (*Cyperus iria*), and gramineous weeds such as barnyardgrass (Echinochloacrusgalli), crabgrass (Digitaria sp.), foxtail (Setaria sp.), green foxtail (Setariaviridis), johnsongrass (Sorghumhalepense), goosegrass (*Eleusine indica*) and Yaseiembaku (Avena fatua).

The compound of the present invention is also effective as a herbicide against annual weeds such as barnyardgrass (Echinochloacrusgalli), small flower flatsedge (Cyperusdifformis) and monochoria (*Monochoria vaginalis*), and perennial weeds such as Sagittaria pygmaea, Sagittaria trifolia, Cyperusserotinus, Eleocharis-kuroguwai, bulrush (Scirpushotarui) and Alismacanaliculatum, grown in paddy fields.

What is claimed is:
1. A picolinic acid derivative of the formula:

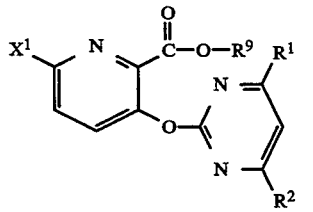

(I)

wherein each of $R^1$ and $R^2$ is an alkoxy group;
$X^1$ is a group of the formula

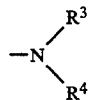

wherein $R^3$ is a hydrogen atom, an alkyl group, a haloalkyl group, an alkoxyalkyl group, an alkenyl group, an alkynyl group, an alkylcarbonyl group, a benzyloxycarbonyl group or a phenylsulfonyl group; and $R^4$ is a haloalkyl group, an alkoxyalkyl group, an alkoxyalkyloxyalkyl group, an alkoxycarbonylalkyl group, a benzyloxyalkyl group, an alkyloxyoxyalkyl group, a phenoxyalkyl group, a dialkylaminoalkyl group, a cyanoalkyl group, an alkoxy group, a cycloalkyl group, an alkenyl group (which may be substituted at one or more positions by a halogen atom or a cyano group), an alkynyl group, a phenylalkyl group (which may be the same or different, and substituted at one or more positions by a halogen atom, an alkyl group, an alkoxy group, a nitro group or a cyano group), a cycloalkylcarbonyl group, a haloalkylcarbonyl group, an alkoxyalkylcarbonyl group, a cyanoalkylcarbonyl group, a phenoxyalkylcarbonyl group, a phenylalkylcarbonyl group, a halophenylalkylcarbonyl group, a benzoyl group (which is substituted by an alkyl group, a haloalkyl group, a halogen atom, an alkoxy group, a cyano group or a nitro group), a furylcarbonyl group, a pyridylcarbonyl group, a pyrrolylcarbonyl group, a thienylcarbonyl group, an alkenylcarbonyl group, a phenylalkenylcarbonyl group, a hydroxycarbonylalkenylcarbonyl group, an alkoxycarbonylalkylcarbonyl group, an alkoxyalkoxycarbonyl group, a monoalkylaminocarbonyl group, a dialkylaminocarbonyl group, a phenylaminocarbonyl group, a benzylaminocarbonyl group, a halobenzylaminocarbonyl group, an alkoxycarbonyl group, a haloalkoxycarbonyl group, a benzyloxycarbonyl group, an alkenyloxycarbonyl group, an alkynyloxycarbonyl group, an alkylsulfonyl group, a haloalkylsulfonyl group, a benzylsulfonyl group which may be substituted by an alkoxycarbonyl group, a phenylsulfonyl group which may be substituted by an alkoxycarbonyl group, a halophenylsulfonyl group, an alkyl(thiocarbonyl) group, a haloalkyl(thiocarbonyl) group, a benzyl(thiocarbonyl) group, a halobenzyl(thiocarbonyl) group, an alkenyl(thiocarbonyl) group, an alkynyl(thiocarbonyl) group which may be substituted by a cyano group, an alkylamino(thiocarbonyl) group, a phenylamino(thiocarbonyl) group, a dialkylamino(thiocarbonyl) group, a benzyloxy group or a group of the formula

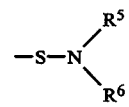

wherein each of $R^5$ and $R^6$ which may be the same or different, is a hydrogen atom, an alkyl group or an alkoxycarbonyl group, or $R^5$ and $R^6$ form together with the adjacent nitrogen atom a morpholino group; or $R^3$ and $R^4$ form together with the adjacent nitrogen atom, an azido group, an isothiocyanate group, a phthalimide group, a maleimide group, a succinimido group, a pyrrolidinyl group, a piperidino group, a pyrrolyl group, a morpholino group, a group of the formula

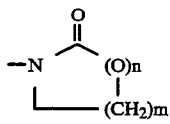

wherein n is 0 or 1, and m is 1 or 2, or
$X^1$ is a group of the formula

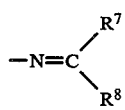

wherein each of $R^7$ and $R^8$ which may be the same or different, is a hydrogen atom, an alkyl group, a dialkylamino group, an amino group, an alkylthio group, a phenyl group or a benzyl group; and $R^9$ is a hydrogen atom, an alkyl group, an alkenyl group, a benzyl group, an alkali metal atom, an alkaline earth metal atom or an organic amine cation; or a salt thereof, wherein said alkyl and alkoxy groups are $C_{1-5}$ linear or branched alkyl and alkoxy groups, said alkenyl and alkynyl groups are $C_{2-6}$ alkenyl and alkynyl groups, said cycloalkyl groups are $C_{3-6}$ cycloalkyl groups, said alkylideneamino groups are $C_{3-12}$ alkylideneamino groups, and said cycloalkylideneamino groups are $C_{3-8}$ cycloalkylideneamino groups.

2. A herbicidal composition comprising a herbicidally effective amount of a picolinic acid derivative of the formula (I) or a salt thereof as defined in claim 1 and an agricultural adjuvant.

3. A picolinic acid derivative of the formula:

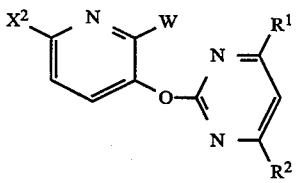

wherein each of $R^1$ and $R^2$ is an alkoxy group, $X^2$ is an amino group, an alkylamino group or a dialkylamino group, and W is $COOR^{10}$, $COSR^{11}$, or $CON(R^{12})(R^{13})$, wherein $R^{10}$ is a phenyl group (which may be substituted by a halogen atom or a methyl group), a benzyloxyalkyl group, an alkylideneamino group, a cycloalkylideneamino group or a dialkylamino group, $R^{11}$ is an alkyl group or a phenyl group, and each of $R^{12}$ and $R^{13}$ which may be the same or different, is a hydrogen atom, an alkylsulfonyl group, an alkoxyalkyl group, an alkyl group, a benzyloxy group or an alkoxy group, or $R^{12}$ and $R^{13}$ form together with the adjacent nitrogen atom, an imidazolyl group; or a salt thereof, wherein said alkyl and alkoxy groups are $C_{1-5}$ linear or branched alkyl and alkoxy groups, said alkenyl and alkynyl groups are $C_{2-6}$ alkenyl and alkynyl groups, said cycloalkyl groups are $C_{3-8}$ cycloalkyl groups, said alkylideneamino groups are $C_{3-12}$ alkylideneamino groups, and said cycloalkylideneamino groups are $C_{3-8}$ cycloalkylideneamino groups.

4. A herbicidal composition comprising a herbicidally effective amount of a picolinic acid derivative of the formula (II) or a salt thereof as defined in claim 3 and an agricultural adjuvant.

5. A picolinic acid derivative of the formula:

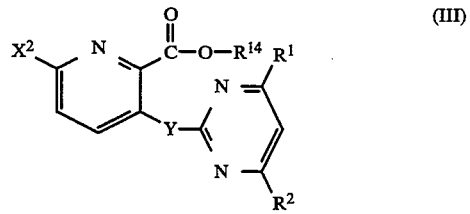

wherein each of $R^1$ and $R^2$ is an alkoxy group, $X^2$ is an amino group, an alkylamino group or a dialkylamino group, Y is a methylene group which may be substituted by a cyano group, or a carbonyl group, and $R^{14}$ is a hydrogen atom or an alkyl group; or a salt thereof, wherein said alkyl and alkyl groups are $C_{1-5}$ linear or branched alkyl and alkoxy groups.

6. A herbicidal composition comprising a herbicidally effective amount of a picolinic acid derivative of the formula (III) or a salt thereof as defined in claim 5 and an agricultural adjuvant.

7. A picolinic acid derivative of the formula:

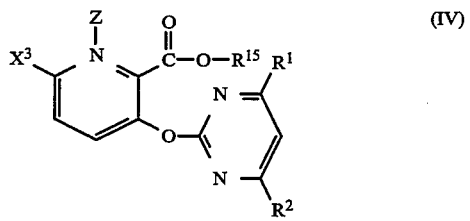

wherein each of $R^1$ and $R^2$ is an alkoxy group, $X^3$ is a dialkylamino group, Z is a group of the formula $R^+A^-$ wherein $R^+$ is a cation selected from the group consisting of an alkyl group, an acyl group and an alkylsulfonyl group, and $A^-$ is an anion of the conjugate base, and $R^{15}$ is an alkyl group; or a salt thereof, wherein said alkyl and alkoxy groups are $C_{1-5}$ linear or branched alkyl and alkoxy groups and said acyl group is a $C_{2-8}$ acyl group.

8. A herbicidal composition comprising a herbicidally effective amount of a picolinic acid derivative of the formula (IV) or a salt thereof as defined in claim 7 and an agricultural adjuvant.

* * * * *